United States Patent
Vollmers et al.

(10) Patent No.: US 11,511,089 B2
(45) Date of Patent: *Nov. 29, 2022

(54) SYSTEMS AND METHODS FOR TREATING PULMONARY HYPERTENSION

(71) Applicant: Aria CV, Inc., St. Paul, MN (US)

(72) Inventors: Karl Vollmers, Minneapolis, MN (US); John Scandurra, St. Paul, MN (US)

(73) Assignee: Aria CV, Inc., St. Paul, MN (US)

( * ) Notice: Subject to any disclaimer, the term of this patent is extended or adjusted under 35 U.S.C. 154(b) by 236 days.

This patent is subject to a terminal disclaimer.

(21) Appl. No.: 16/900,794

(22) Filed: Jun. 12, 2020

(65) Prior Publication Data

US 2020/0306435 A1 Oct. 1, 2020

Related U.S. Application Data

(63) Continuation of application No. 15/785,304, filed on Oct. 16, 2017, now Pat. No. 10,682,448, which is a
(Continued)

(51) Int. Cl.
*A61M 25/10* (2013.01)
*A61M 39/02* (2006.01)
(Continued)

(52) U.S. Cl.
CPC ....... *A61M 25/104* (2013.01); *A61B 17/1204* (2013.01); *A61B 17/12036* (2013.01);
(Continued)

(58) Field of Classification Search
CPC .......................... A61M 1/1086; A61M 1/1044
(Continued)

(56) References Cited

U.S. PATENT DOCUMENTS 3,275,001 A 9/1966 Rosecrans
3,634,924 A 1/1972 Blake et al.
(Continued)

FOREIGN PATENT DOCUMENTS

CN 102657910.1 A 9/2012
CN 103260547 A 8/2013
(Continued)

OTHER PUBLICATIONS

U.S. Appl. No. 13/701,721 / U.S. Pat. No. 9,987,153, filed May 31, 2011 / Jun. 5, 2018.
(Continued)

*Primary Examiner* — Nadia A Mahmood
(74) *Attorney, Agent, or Firm* — Eversheds Sutherland (US) LLP; Christopher C. Bolten; Albert K. Heng

(57) ABSTRACT

A system for treating heart disease, such as pulmonary hypertension or right heart failure, including an implantable component and external components for monitoring the implantable component is provided. The implantable component may include a compliant member, e.g., balloon, coupled to a reservoir via a conduit. Preferably, the compliant member is adapted to be implanted in a pulmonary artery and the reservoir is adapted to be implanted subcutaneously. The external components may include a clinical controller component, monitoring software configured to run a clinician's computer, a patient monitoring device, and a mobile application configured to run on a patient's mobile device.

21 Claims, 15 Drawing Sheets

Related U.S. Application Data continuation of application No. 15/474,902, filed on Mar. 30, 2017, now Pat. No. 9,801,989, which is a continuation of application No. 14/990,627, filed on Jan. 7, 2016, now Pat. No. 9,610,391, which is a continuation of application No. 14/710,180, filed on May 12, 2015, now Pat. No. 9,242,082, which is a continuation of application No. 14/531,846, filed on Nov. 3, 2014, now Pat. No. 9,039,725, which is a continuation of application No. 14/309,758, filed on Jun. 19, 2014, now Pat. No. 8,876,850.

(51) Int. Cl.

| | | |
|---|---|---|
| A61M 5/172 | (2006.01) | |
| A61B 17/12 | (2006.01) | |
| A61M 60/135 | (2021.01) | |
| A61M 60/869 | (2021.01) | |
| A61M 60/585 | (2021.01) | |
| A61M 60/523 | (2021.01) | |
| A61M 60/295 | (2021.01) | |
| A61M 60/538 | (2021.01) | |
| A61M 60/515 | (2021.01) | |
| A61M 5/50 | (2006.01) | |
| A61M 25/04 | (2006.01) | |
| A61M 25/06 | (2006.01) | |
| A61M 29/02 | (2006.01) | |
| A61B 17/00 | (2006.01) | |
| A61B 90/00 | (2016.01) | |

(52) U.S. Cl.
CPC ..... *A61B 17/12136* (2013.01); *A61M 5/1723* (2013.01); *A61M 5/5086* (2013.01); *A61M 25/04* (2013.01); *A61M 25/0662* (2013.01); *A61M 29/02* (2013.01); *A61M 39/0208* (2013.01); *A61M 60/135* (2021.01); *A61M 60/295* (2021.01); *A61M 60/515* (2021.01); *A61M 60/523* (2021.01); *A61M 60/538* (2021.01); *A61M 60/585* (2021.01); *A61M 60/869* (2021.01); *A61B 2017/00022* (2013.01); *A61B 2017/00212* (2013.01); *A61B 2017/00221* (2013.01); *A61B 2090/064* (2016.02); *A61M 2025/0681* (2013.01); *A61M 2205/04* (2013.01); *A61M 2205/18* (2013.01); *A61M 2205/3324* (2013.01); *A61M 2205/3327* (2013.01); *A61M 2205/3334* (2013.01); *A61M 2205/3368* (2013.01); *A61M 2205/3389* (2013.01); *A61M 2205/3515* (2013.01); *A61M 2205/3523* (2013.01); *A61M 2205/505* (2013.01); *A61M 2210/12* (2013.01); *A61M 2230/04* (2013.01)

(58) Field of Classification Search
USPC .......................................................... 606/194
See application file for complete search history.

(56) References Cited

U.S. PATENT DOCUMENTS

| | | | |
|---|---|---|---|
| 3,818,903 | A | 6/1974 | Bleecker |
| 4,422,447 | A | 12/1983 | Schiff |
| 4,793,351 | A | 12/1988 | Landman et al. |
| 4,902,273 | A | 2/1990 | Choy et al. |
| 4,938,766 | A | 7/1990 | Jarvik |
| 4,955,905 | A | 9/1990 | Reed |
| 5,002,531 | A | 3/1991 | Bonzel |
| 5,112,303 | A | 5/1992 | Pudenz et al. |
| 5,222,980 | A | 6/1993 | Gealow |
| 5,409,444 | A | 4/1995 | Kensey et al. |
| 5,486,192 | A | 1/1996 | Walinsky et al. |
| 5,496,311 | A | 3/1996 | Abele et al. |
| 5,578,085 | A | 11/1996 | Johnson, Jr. et al. |
| 5,713,867 | A | 2/1998 | Morris |
| 5,769,821 | A | 6/1998 | Abrahamson et al. |
| 5,795,325 | A | 8/1998 | Valley et al. |
| 5,814,016 | A | 9/1998 | Valley et al. |
| 5,820,542 | A | 10/1998 | Dobak et al. |
| 5,833,655 | A | 11/1998 | Freed et al. |
| 6,017,324 | A | 1/2000 | Tu et al. |
| 6,030,336 | A | 2/2000 | Franchi |
| 6,053,891 | A | 4/2000 | Decampli |
| 6,136,025 | A | 10/2000 | Barbut et al. |
| 6,210,318 | B1 | 4/2001 | Lederman |
| 6,261,304 | B1 | 7/2001 | Hall et al. |
| 6,461,367 | B1 | 10/2002 | Kirsch et al. |
| 6,558,349 | B1 | 5/2003 | Kirkman |
| 6,559,349 | B1 | 5/2003 | Slaugh et al. |
| 6,576,007 | B2 | 6/2003 | Dehdashtian et al. |
| 6,579,224 | B1 | 6/2003 | Burton et al. |
| 6,682,473 | B1 | 1/2004 | Matsuura et al. |
| 7,044,967 | B1 | 5/2006 | Solem et al. |
| 7,074,178 | B2 | 7/2006 | Connors et al. |
| 7,468,050 | B1 | 12/2008 | Kantrowitz |
| 7,540,876 | B2 | 6/2009 | Connors et al. |
| 7,766,814 | B2 | 8/2010 | Walsh |
| 7,811,249 | B2 | 10/2010 | Saab |
| 7,928,367 | B2 | 4/2011 | Hirota et al. |
| 8,016,740 | B2 | 9/2011 | Connors et al. |
| 8,092,521 | B2 | 1/2012 | Figulla et al. |
| 8,116,883 | B2 | 2/2012 | Williams et al. |
| 8,206,378 | B1 | 6/2012 | Kalpin et al. |
| 8,585,572 | B2 | 11/2013 | Mehmanesh |
| 8,747,386 | B2 | 6/2014 | Rykhus et al. |
| 8,876,850 | B1 | 11/2014 | Vollmers et al. |
| 8,882,653 | B2 | 11/2014 | Gillespie, Jr. et al. |
| 8,956,379 | B2 | 2/2015 | Luciano et al. |
| 9,017,359 | B2 | 4/2015 | Scandurra et al. |
| 9,039,725 | B1 | 5/2015 | Vollmers et al. |
| 9,107,992 | B2 | 8/2015 | Kushwaha et al. |
| 9,242,082 | B2 | 1/2016 | Vollmers et al. |
| 9,333,328 | B2 | 5/2016 | Scandurra et al. |
| 9,610,391 | B2 | 4/2017 | Vollmers et al. |
| 9,801,989 | B2 | 10/2017 | Vollmers et al. |
| 9,987,153 | B2 | 6/2018 | Scandurra et al. |
| 10,327,880 | B2 | 6/2019 | Connors et al. |
| 10,350,397 | B2 | 7/2019 | Scandurra et al. |
| 10,376,681 | B2 | 8/2019 | Bak-Boychuk et al. |
| 10,617,538 | B2 | 4/2020 | Scandurra et al. |
| 10,682,448 | B2 | 6/2020 | Vollmers et al. |
| 10,702,682 | B2 | 7/2020 | Scandurra et al. |
| 10,751,519 | B2 | 8/2020 | Scandurra et al. |
| 11,141,581 | B2 | 10/2021 | Vollmers et al. |
| 11,331,105 | B2 | 5/2022 | Gainor et al. |
| 2001/0023332 | A1 | 9/2001 | Hahnen |
| 2003/0055465 | A1 | 3/2003 | Ben-Haim et al. |
| 2003/0208259 | A1 | 11/2003 | Penhasi |
| 2004/0093007 | A1 | 5/2004 | Sussman et al. |
| 2004/0106971 | A1 | 6/2004 | Schwartz et al. |
| 2004/0111006 | A1 | 6/2004 | Alferness et al. |
| 2004/0143319 | A1 | 7/2004 | Schwartz et al. |
| 2004/0210304 | A1 | 10/2004 | Seguin et al. |
| 2005/0015107 | A1 | 1/2005 | O'Brien |
| 2005/0059965 | A1 | 3/2005 | Eberl et al. |
| 2005/0070938 | A1 | 3/2005 | Copa et al. |
| 2005/0131451 | A1 | 6/2005 | Kleshinski et al. |
| 2005/0251175 | A1* | 11/2005 | Weisenburgh, II .. A61B 17/068 606/153 |
| 2005/0267596 | A1 | 12/2005 | Chen et al. |
| 2006/0085028 | A1 | 4/2006 | Boock |
| 2006/0093642 | A1 | 5/2006 | Ranade |
| 2006/0106450 | A1 | 5/2006 | Ben Muvhar |
| 2006/0129083 | A1 | 6/2006 | Brenneman et al. |
| 2006/0135962 | A1 | 6/2006 | Kick et al. |
| 2006/0155310 | A1 | 7/2006 | Binmoeller |
| 2006/0241745 | A1 | 10/2006 | Solem |
| 2006/0253095 | A1 | 11/2006 | Stull |
| 2007/0142819 | A1 | 6/2007 | El-Nounou et al. |
| 2007/0156013 | A1 | 7/2007 | Birk |

(56) References Cited

U.S. PATENT DOCUMENTS

| | | |
|---|---|---|
| 2007/0156167 A1 | 7/2007 | Connors et al. |
| 2007/0293848 A1 | 12/2007 | Endo et al. |
| 2008/0114338 A1 | 5/2008 | Kumar |
| 2008/0132750 A1 | 6/2008 | Miller |
| 2008/0147181 A1 | 6/2008 | Ghione et al. |
| 2008/0194905 A1 | 8/2008 | Walsh |
| 2008/0195174 A1 | 8/2008 | Walker et al. |
| 2008/0243093 A1 | 10/2008 | Kalpin et al. |
| 2008/0312679 A1 | 12/2008 | Hardert et al. |
| 2009/0143837 A1 | 6/2009 | Rossing et al. |
| 2009/0222083 A1 | 9/2009 | Nguyen et al. |
| 2009/0240277 A1 | 9/2009 | Connors et al. |
| 2009/0294031 A1 | 12/2009 | Pepper et al. |
| 2010/0042070 A1 | 2/2010 | Gill et al. |
| 2010/0099945 A1 | 4/2010 | Birk et al. |
| 2010/0185049 A1 | 7/2010 | Birk et al. |
| 2010/0197994 A1 | 8/2010 | Mehmanesh |
| 2010/0204590 A1 | 8/2010 | Hatib et al. |
| 2010/0274221 A1 | 10/2010 | Sigg et al. |
| 2010/0324472 A1 | 12/2010 | Wulfman |
| 2010/0331767 A1 | 12/2010 | Frankowski et al. |
| 2011/0124951 A1 | 5/2011 | Walsh |
| 2011/0137210 A1 | 6/2011 | Johnson |
| 2011/0137428 A1 | 6/2011 | Terliuc |
| 2012/0053514 A1 | 3/2012 | Robinson et al. |
| 2012/0083646 A1 | 4/2012 | Benson |
| 2012/0172654 A1 | 7/2012 | Bates |
| 2013/0079871 A1 | 3/2013 | Scandurra et al. |
| 2013/0165964 A1 | 6/2013 | Vollmers et al. |
| 2013/0245665 A1 | 9/2013 | Scandurra et al. |
| 2014/0214149 A1 | 7/2014 | Kuraguntla et al. |
| 2014/0228878 A1 | 8/2014 | Scandurra et al. |
| 2014/0370246 A1 | 12/2014 | Hurt |
| 2015/0196303 A1 | 7/2015 | Seguin |
| 2015/0216531 A1 | 8/2015 | Seguin |
| 2015/0282859 A1 | 10/2015 | Bencini et al. |
| 2015/0352335 A1 | 12/2015 | Moeller |
| 2015/0366652 A1 | 12/2015 | Connors |
| 2016/0144091 A1 | 5/2016 | Breedon et al. |
| 2016/0237237 A1 | 8/2016 | Tour et al. |
| 2016/0310306 A1 | 10/2016 | Brister et al. |
| 2018/0036464 A1 | 2/2018 | Vollmers et al. |
| 2019/0192835 A1 | 6/2019 | Scandurra et al. |
| 2020/0046369 A1 | 2/2020 | Gainor et al. |
| 2020/0306435 A1 | 10/2020 | Vollmers et al. |
| 2020/0368507 A1 | 11/2020 | Scandurra et al. |
| 2021/0069396 A1 | 3/2021 | Vollmers et al. |

FOREIGN PATENT DOCUMENTS

| | | |
|---|---|---|
| DE | 19508129 A1 | 9/1996 |
| DE | 19508129 C2 | 2/1997 |
| DE | 10 2005 060 197 A1 | 6/2007 |
| EP | 0 366 814 A1 | 5/1990 |
| EP | 0 959 912 B1 | 12/1999 |
| EP | 0959912 B1 | 9/2004 |
| EP | 2 016 961 B1 | 1/2009 |
| EP | 2016961 A1 | 1/2009 |
| FR | 3017044 A1 | 8/2015 |
| FR | 3016279 A1 | 7/2017 |
| JP | 2005538807 A | 12/2005 |
| JP | 2007526039 A | 9/2007 |
| JP | 2009502247 A | 1/2009 |
| JP | 2009509650 A | 3/2009 |
| WO | WO-90/04430 A1 | 5/1990 |
| WO | WO-90/06086 A1 | 6/1990 |
| WO | WO-93/17731 A1 | 9/1993 |
| WO | WO-95/10317 A1 | 4/1995 |
| WO | WO-95/32018 A1 | 11/1995 |
| WO | WO-96/00095 A1 | 1/1996 |
| WO | WO-96/12518 A1 | 5/1996 |
| WO | WO-96/34647 A1 | 5/1996 |
| WO | WO-98/50100 A1 | 11/1998 |
| WO | WO-99/04833 A1 | 2/1999 |
| WO | WO-00/66030 A1 | 11/2000 |
| WO | WO-02/36048 A1 | 5/2002 |
| WO | WO-2004/026112 A2 | 4/2004 |
| WO | WO-2004/080338 A2 | 9/2004 |
| WO | WO-2005/084730 A1 | 9/2005 |
| WO | WO-2006/020942 A1 | 2/2006 |
| WO | WO-2006/067473 A1 | 6/2006 |
| WO | WO-2007/014028 A1 | 2/2007 |
| WO | WO-2007/038476 A2 | 4/2007 |
| WO | WO-2007/059594 A1 | 5/2007 |
| WO | WO-2008/154145 A1 | 12/2008 |
| WO | WO-2010/022173 A1 | 2/2010 |
| WO | WO-2010/129089 A4 | 11/2010 |
| WO | WO-2010129089 A2 | 11/2010 |
| WO | WO-2012/071395 A1 | 5/2012 |
| WO | WO-2013/109891 A | 7/2013 |
| WO | WO-2013/148697 A1 | 10/2013 |
| WO | WO-2013/185138 A1 | 12/2013 |
| WO | WO-2015/107434 A1 | 7/2015 |
| WO | WO-2015102693 A2 | 7/2015 |
| WO | WO-2015/114471 A1 | 8/2015 |
| WO | WO-2015/133849 A1 | 9/2015 |
| WO | WO-2018/075552 A1 | 4/2018 |

OTHER PUBLICATIONS

U.S. Appl. No. 13/884,169 / U.S. Pat. No. 9,017,359, filed Nov. 22, 2011 / Apr. 28, 2015.
U.S. Appl. No. 14/253,127 / U.S. Pat. No. 9,333,328, filed Apr. 15, 2014 / May 10, 2016.
U.S. Appl. No. 14/309,758 / U.S. Pat. No. 8,876,850, filed Jun. 19, 2014 / Nov. 4, 2014.
U.S. Appl. No. 14/531,846 / U.S. Pat. No. 9,039,725, filed Nov. 3, 2014 / May 26, 2015.
U.S. Appl. No. 14/710,180 / U.S. Pat. No. 9,242,082, filed May 12, 2015 / Jan. 26, 2016.
U.S. Appl. No. 14/955,109, filed Dec. 1, 2015.
U.S. Appl. No. 14/956,127 /U.S. Pat. No. 10,350,397, filed Dec. 1, 2015 / Jul. 16, 2019.
U.S. Appl. No. 14/990,627 / U.S. Pat. No. 9,610,391, filed Jan. 7, 2016 / Apr. 4, 2017.
U.S. Appl. No. 15/474,902 / U.S. Pat. No. 9,801,989, filed Mar. 30, 2017 / Oct. 31, 2017.
U.S. Appl. No. 15/785,304 / U.S. Pat. No. 10,682,448, filed Oct. 16, 2017 / Jun. 16, 2020.
U.S. Appl. No. 15/993,572 / U.S. Pat. No. 10,617,538, filed May 30, 2018 / Apr. 14, 2020.
U.S. Appl. No. 16/288,088, filed Feb. 27, 2019.
U.S. Appl. No. 16/342,968, filed Apr. 17, 2019.
U.S. Appl. No. 16/842,612, filed Apr. 7, 2020.
"Aria CV Wins Contest for Pulmonary Arterial Hypertension Medical Device," https://pulmonaryhypertensionnews.com/2018/09/27/aria-cv-wins-contest-pulmonary-arterial-hypertension-medical-device/, dated Sep. 27, 2018, (accessed Dec. 13, 2019).
"Aria CV wins top honors in device organization 'Shark Tank' competition," http://www.startribune.com/joe-carlson/271816721, dated Apr. 22, 2019, (accessed Dec. 13, 2019).
"Aria CV Awarded Top Prize At TCT's 2018 Shark Tank Competition", https://cathlabdigest.com/content/Ara-CV-Awarded-Top-Prize-TCT's-2018-Shark-Tank-Competition, dated Oct. 9, 2018, (accessed Dec. 13, 2019).
Borlaug, B. A., & Kass, D. A., "Ventricular-Vascular Interaction in Heart Failure," Heart Failure Clinics, 4(1):23-36 (2008).
Brian, Jr., M.D., Johnny E., "Gas Exchange, Partial Pressure Gradients, and the Oxygen Window," Department of Anesthesia, University of Iowa College of Medicine, 1-16 (Oct. 2001).
Elzinga, G., et al. "Pressure and flow generated by the left ventricle against different impedances," Circ Res. 32(2):178-186 (1973).
Elzinga, G., et al., "Left and right ventricular pump function and consequences of having two pumps in one heart. A study on the isolated cat heart." Circ Res, 46:564-574 (1980).
Extended EP Search Report dated Feb. 6, 2018 in EP Patent Appl. Serial No. 11843546.0.
Extended EP Search Report dated Mar. 1, 2017 in EP Patent Application Serial No. 11792905.9.

(56) References Cited

OTHER PUBLICATIONS

Extended EP Search Report dated Jun. 19, 2019 in EP Patent Application Serial No. 19165162.9.
Grant, B. J. B., et al., "Clinical significance of pulmonary arterial input impedance," Eur Respir J. 9(11):2196-2199 (1996).
Harnek, J., et al., "Transcatheter Implantation of the MONARC Coronary Sinus Device for Mitral Regurgitation: 1-year Results From the EVOLUTION Phase I Study (Clinical Evaluation of the Edwards Lifesciences Percutaneous Mitral Annuloplasty System for the Treatment of Mitral Regurgitation)," JACC: Cardiovascular Interventions, 4(1):115-122 (2011).
International Search Report & Written Opinion dated Dec. 22, 2015 in Int'l PCT Patent Application Serial No. PCT/US2015/036201.
International Search Report & Written Opinion dated Jan. 31, 2018 in Int'l PCT Patent Application Serial No. PCT/US2017/057035.
International Search Report & Written Opinion dated Sep. 8, 2011 in Int'l PCT Patent Application Serial No. PCT/US2011/38558.
Lammers, S. et al., "Mechanics and Function of the Pulmonary Vasculature: Implications for Pulmonary Vascular Disease and Right Ventricular Function," Comprehensive Physiology, 2:295-319 (2012).
Lankhaar, J. W., et al., "Pulmonary vascular resistance and compliance stay inversely related during treatment of pulmonary hypertension," European Heart Journal, 29:1688-1695 (2008).
Lategola, Michael T., "Measurement of total pressure of dissolved gas in mammalian tissue In vivo," J. Appl. Physiol., 19(2):322-324 (1964).
Loring, S. H., et al., "Gas exchange in body cavities," Handbook of Physiology—The Respiratory System IV, Chapter 15, pp. 283-295 (1987).
Mahapatra, S. et al., "Relationship of Pulmonary Arterial Capacitance and Mortality in Idiopathic Pulmonary Arterial Hypertension," J. Am. Coll. Cardiol., 47:799-803 (2006).
Naeije, R., et al., "Right ventricular function in pulmonary hypertension: physiological concepts," European Heart Journal Supplements 9 (Supplement H) H5-H9 (2007).
PCT International Search Report & Written Opinion dated Mar. 24, 2015 in Int'l PCT Application Serial No. PCT/IB/2015/050066.
PCT International Search Report & Written Opinion dated Mar. 24, 2015 n Int'l PCT Application Serial No. PCT/IB/2015/050068.
PCT International Search Report & Written Opinion dated Mar. 8, 2012 in Int'l PCT Patent Application No. PCT/US2011/061815.
Pellegrini, P., et al., "Prognostic Relevance of Pulmonary Arterial Compliance in Patients With Chronic Heart Failure," CHEST Journal, 145(5):1064-1070 (2014).
Piiper, J., "Physiological equilibria of gas cavities in the body," Handbook of Physiology—Respiration II, Chapter 48, 1205-1218 (1965).
Procyrion, "A tool for the Cardiologist," published Jul. 3, 2013. http://web.archive.org/web/20130703020540/http://www.procyrion.com/technology.
Reuben, S. R., "Compliance of the Human Pulmonary Arterial System in Disease," Circulation Research, 29:40-50 (1971).
Saouti, N., et al., "The arterial load in pulmonary hypertension," Eur Respir Rev., 19(117):197-203 (2010).
PCT Second Written Opinion dated Jul. 7, 2016 in Int'l PCT Patent Application Serial No. PCT/US2015/036201.
Souza, R. "Assessment of compliance in pulmonary arterial hypertension," European Heart Journal, 29:1603-1604, (2008).
Sunagawa, K., et. al., "Left ventricular interaction with arterial load studied in isolated canine ventricle," Am. J. of Physiol. 245 (Heart Circ. Physiol. 14), H773-H780 (1983).
Tenney, et al., "Gas Transfers in a Sulfur Hexafluoride Pneumoperitoneum," Journal of Applied Physiology, 6(4):201-208 (1953).
Tucker, et al., "Inert Gas Exchange in Subcutaneous Gas Pockets of Air-Breathing Animals: Theory and Measurement," Respiration Physiology, 1:151-171 (1966).
Wang, Z., et al., "Pulmonary vascular wall stiffness: An important contributor to the increased right ventricular afterload with pulmonary hypertension," Pulmonary Circulation, 1(2):212-223 (2011).

* cited by examiner

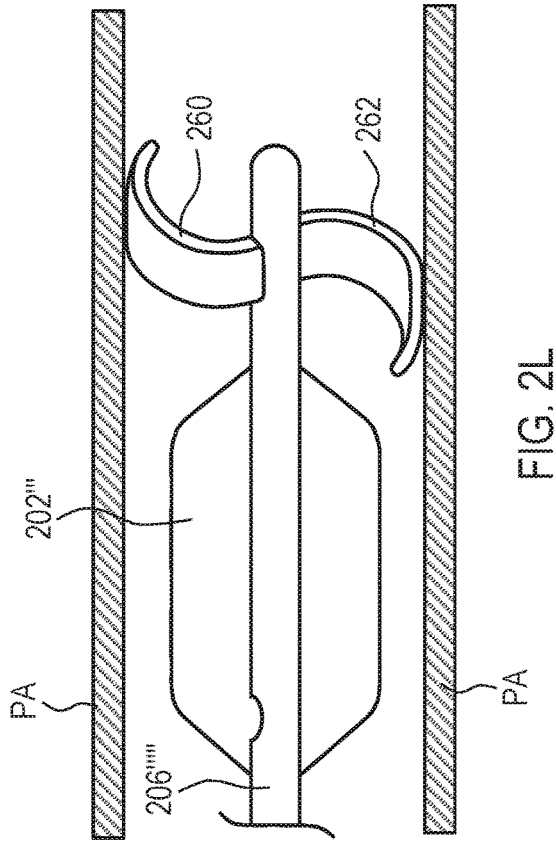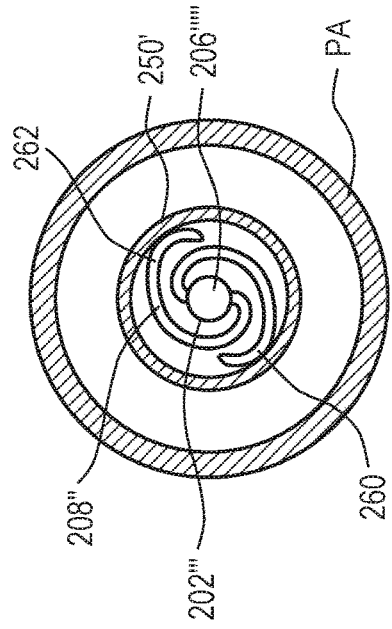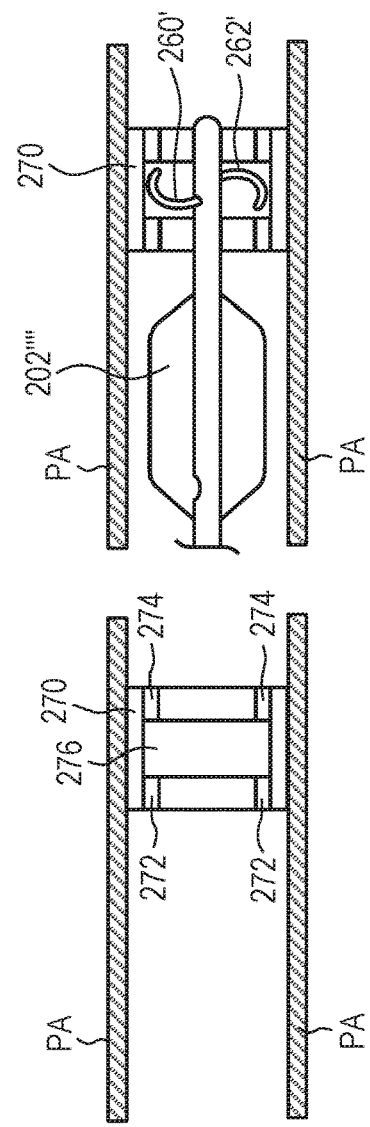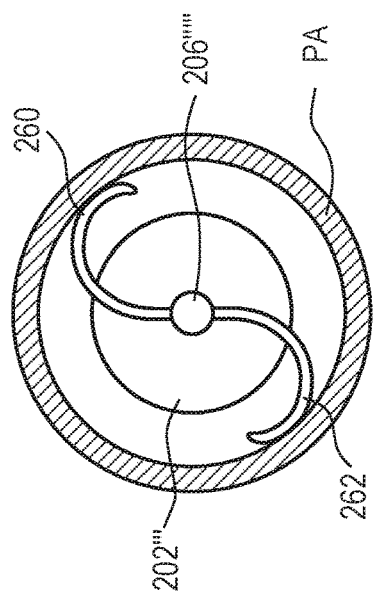

SYSTEMS AND METHODS FOR TREATING PULMONARY HYPERTENSION

I. CROSS-REFERENCE TO RELATED APPLICATIONS

This application is a continuation of U.S. patent application Ser. No. 15/785,304, filed Oct. 16, 2017, now U.S. Pat. No. 10,682,448, which is a continuation of U.S. patent application Ser. No. 15/474,902, filed Mar. 30, 2017, now U.S. Pat. No. 9,801,989, which is a continuation of U.S. patent application Ser. No. 14/990,627, filed Jan. 7, 2016, now U.S. Pat. No. 9,610,391, which is a continuation of U.S. patent application Ser. No. 14/710,180, filed May 12, 2015, now U.S. Pat. No. 9,242,082, which is a continuation of U.S. patent application Ser. No. 14/531,846, filed Nov. 3, 2014, now U.S. Pat. No. 9,039,725, which is a continuation of U.S. patent application Ser. No. 14/309,758, filed Jun. 19, 2014, now U.S. Pat. No. 8,876,850, the entire contents of each of which are incorporated herein by reference.

II. FIELD OF THE INVENTION

This application generally relates to systems and methods for treating pulmonary hypertension, including implantable devices for reducing pulsatile load in the pulmonary artery and external devices for monitoring the implantable devices.

III. BACKGROUND OF THE INVENTION

Pulmonary hypertension (PH) is defined as a rise in mean pressure in the main pulmonary artery. PH may arise from many different causes, but, in all patients, has been shown to increase mortality rate. A deadly form of PH arises in the very small branches of the pulmonary arteries and is known as Pulmonary Arterial Hypertension (PAH). In PAH, the cells inside the small arteries multiply due to injury or disease, decreasing the area inside of the artery and thickening the arterial wall. As a result, these small pulmonary arteries narrow and stiffen, causing blood flow to become restricted and upstream pressures to rise. This increase in pressure in the main pulmonary artery is the common connection between all forms of PH regardless of underlying cause.

PH causes the larger pulmonary arteries to stretch and stiffen. As a stroke volume of blood is delivered to the main pulmonary artery, the artery is already stretched and will not further expand. The lack of expansion causes a much larger rise in pressure with each heartbeat (called systolic or peak pressure) than would occur in a healthy, compliant vessel that could stretch to accommodate the stroke volume. In between heart beats, the arteries in a diseased patient do not contract as they normally would and diastolic pressure and flow through the lungs drops causing a reduction in cardiac output. The heart has to work harder to push the same stroke volume of blood into the stiff artery at a higher pressure. At the same time, the high pulse pressure travels down the pulmonary arteries to the small vessels and activates molecular signaling pathways causing the cells to multiply more rapidly, accelerating disease progression.

As the pressure within the pulmonary artery increases, the right side of the heart enlarges and thickens to compensate, but eventually reaches the point where it cannot continue to pump enough blood through the lungs to satisfy the body's need for oxygenated blood. This progressive reduction of blood flow is first noticed as shortness of breath when exercising. Over time, the right ventricular remodeling worsens and patients lose the ability to maintain a normal daily level of activity and enter end stage heart failure where the right ventricle dilates and loses effectiveness reducing blood flow even further. At the end stage, the patient mortality rate is high.

Current treatment protocols for PH and Primary PH include administration of pharmaceuticals. However, such pharmaceuticals are extremely expensive and not sufficiently effective.

Previously known implantable systems having a balloon, conduit, and reservoir have been described. However, such systems suffer from a number of drawbacks for use in treating pulmonary hypertension including the inability to effectively and efficiently monitor operation of the system after implantation.

It would therefore be desirable to provide systems and methods for treating heart disease, such as pulmonary hypertension and right heart failure, where the implantable components may be monitored externally.

IV. SUMMARY OF THE INVENTION

The present disclosure overcomes the drawbacks of previously-known systems by providing systems and methods for treating heart disease, e.g., pulmonary hypertension or right heart failure. The system includes an implantable component and external components for monitoring the implantable component. The implantable component may include a compliant member, e.g., balloon, coupled to a reservoir via a conduit. Preferably, the reservoir is adapted to be implanted subcutaneously and the compliant member is adapted to be implanted in a pulmonary artery, e.g., a diseased, enlarged, and stiff pulmonary artery. The external components may include a clinical controller component, monitoring software configured to run a clinician's computer, a patient monitoring device, and a mobile application configured to run on a patient's mobile device.

The external clinical controller component may include a fluidic connector configured to be coupled to the implantable component, e.g., via the reservoir, to permit fluidic communication with the implantable component. The fluidic connector may be a needle adapted to be inserted transcutaneously into the implantable component, e.g., via insertion of the needle into a septum in the reservoir. In one embodiment, the fluidic connector is a conduit configured to be coupled to a partially implanted conduit that is connected to the implantable component, e.g., at the reservoir. The external clinical controller component also may include one or more sensors, e.g., a pressure transducer, configured to generate signals indicative of parameters, e.g., pressure, within the implantable component. In one embodiment, a pressure transducer is configured to generate a signal indicative of pressure within the reservoir.

The monitoring software may be non-transitory computer readable media configured to run on a computer operatively coupled to the external clinical controller. The non-transitory computer readable media may be configured to cause a graphical user interface to display information indicative of the parameters, e.g., pressure, within the implantable component based on the signals from the sensors.

The external monitoring component may be configured to wirelessly activate one or more sensors, e.g., a pressure sensor, disposed within the implantable component to cause the one or more sensors to sense a parameter, e.g., pressure, within the implantable component. The sensor(s) may be configured to transmit a signal(s), e.g., pressure signal, indicative of the sensed parameter to the external monitoring component. The sensor(s) may be located in or on any part of the implantable component.

The mobile application is configured to run on a mobile device, e.g., smartphone, tablet, laptop, smart watch, or the like. The external monitoring component may be configured to transmit the signal to the mobile device such that the mobile device may display information indicative of the parameter sensed within the implantable component based on the signal. The mobile device may be configured to run a routine to generate an alert if the sensed parameter is above a first predetermined threshold or below a second predetermined threshold.

The external clinical controller component may include a pressure source configured to hold fluid to be injected into the implantable component through the fluidic connector when the fluidic connector is in fluidic communication with the implantable component. In addition, the external clinical controller component may include a fluid movement mechanism, e.g., pump, plunger, configured to move fluid from the pressure source through the fluidic connector and/or to extract fluid from the implantable component through the fluidic connector. The fluid in the pressure source may be pressurized. The fluidic connector lumen(s) may include one or more valves and one or more sensors. The external clinical controller component may have an actuator, e.g., button, trigger, actuation of which causes fluid to move from the pressure source through the fluidic connector, e.g., by opening a valve.

The external clinical controller component may include one or more sensors configured to generate parameter signal (s) indicative of a parameter(s). Parameters may include pressure within the implantable component, temperature within the implantable component, humidity within the implantable component, fluid flow rate within the implantable component, volume of injected fluid from the external clinical controller, volume of extracted fluid from the implantable component, $CO_2$ concentration or other gas or liquid concentration within the implantable component, and pH within the implantable component. The external clinical controller also may be configured to display information indicative of the parameters based on the parameter signals from the sensors. In addition, the non-transitory computer readable media may be configured to cause the graphical user interface to display information indicative of the parameters based on the parameter signals from the sensor and to display a waveform showing pressure versus time based on the signal from the pressure transducer. The non-transitory computer readable media may be configured to run a routine to calculate pulmonary arterial compliance and to cause the graphical user interface to display the calculated pulmonary arterial compliance.

The compliant member may have any suitable shape including a cylindrical shape or a tapered shape configured to reduce billowing of the compliant member. The implantable component may include an anchor configured to secure the compliant member within the pulmonary artery. The anchor may be coupled to the conduit proximal and/or distal to the compliant member and may have any suitable shape, e.g., a plurality of petals. The compliant member may be configured to be detachable from at least a portion of the anchor in vivo such that the compliant member is replaceable while at least the portion of the anchor remains implanted. Preferably, the anchor is configured to be delivered in a contracted state within a sheath and to expand to a deployed state when exposed from the sheath.

In accordance with another aspect of the present disclosure, a method is provided for treating heart disease, e.g., pulmonary hypertension, right heart failure. The method may include providing an implantable component comprising a compliant member, a reservoir, and a conduit; implanting the implantable component such that the compliant member is disposed in a pulmonary artery, the reservoir is disposed subcutaneously, and the conduit is coupled between the compliant member and the reservoir; providing an external clinical controller component comprising a fluidic connector and a pressure transducer; coupling the fluidic connector to the reservoir; measuring pressure within the reservoir using the pressure transducer; transmitting the measured pressure to a computer; and displaying information indicative of the measured pressure on a graphical user interface of the computer.

V. BRIEF DESCRIPTION OF THE DRAWINGS

FIGS. 2J through 2N show alternative anchors for use with the implantable component.

VI. DETAILED DESCRIPTION OF THE INVENTION

Systems and methods of the present disclosure comprise implantable devices for restoring compliance to a portion of a patient's vasculature, such as the pulmonary system, and external devices for adjusting and monitoring parameters of the implantable devices. In accordance with the principles of the present disclosure, the systems may be optimized for use in treating pulmonary hypertension (PH), including Pulmonary Arterial Hypertension (PAH) and Primary PH, and right heart failure (RHF).

Figure 1:
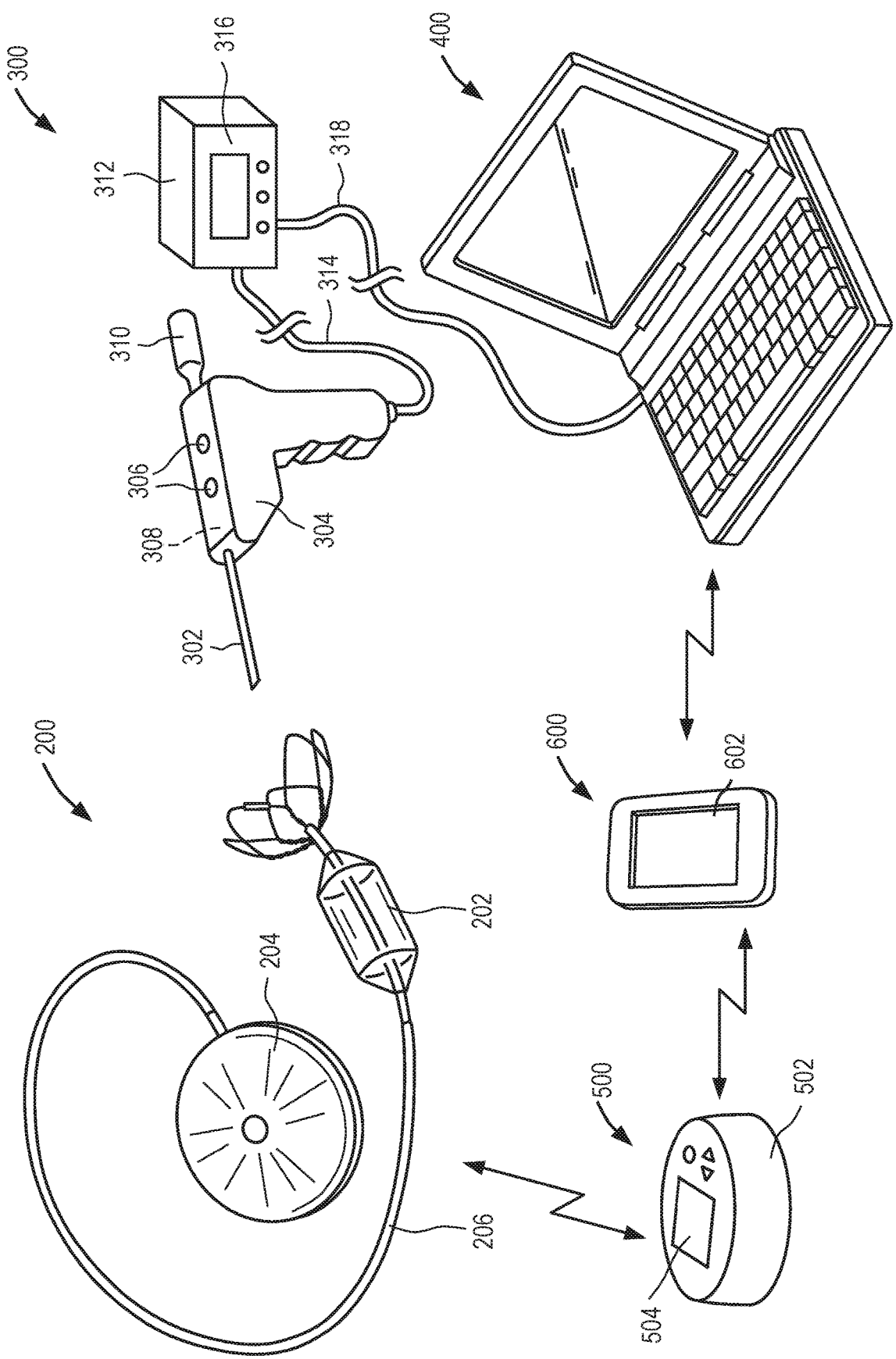
FIG. 1 is a schematic view of an exemplary embodiment of a system constructed in accordance with the principles of the present disclosure.

Referring to FIG. 1, an overview of an exemplary system constructed in accordance with the principles of the present disclosure is provided. In FIG. 1, components of the system are not depicted to scale on either a relative or absolute basis. System 100 may include implantable component 200, external clinical controller component 300, software-based monitoring system 400, external monitoring component 500, and mobile application 600.

Implantable component 200 includes compliant member 202, reservoir 204, and conduit 206. Implantable component 200 may be a closed-loop, passive system and constructed similar to the components described in U.S. Patent Pub. No. 2013/0245665 to Scandurra, assigned to the assignee of the present disclosure, the entire contents of which are incorporated herein by reference. Compliant member 202 is adapted to be implanted in a body lumen, e.g., the pulmonary artery, and reservoir 204 is adapted to be implanted subcutaneously. Conduit 206 is configured to couple compliant member 202 and reservoir 204 such that fluid may flow between compliant member 202 and reservoir 204 via conduit 206 in a closed-loop manner in response to pressure changes in the body lumen during the cardiac cycle. In one embodiment, compliant member 202 is configured to contract during systole and expand during diastole, thereby decreasing peak pressure in the pulmonary artery, improving compliance of the pulmonary artery and the right side of the heart, and reducing remodeling of the pulmonary artery and the right side of the heart.

External clinical controller component 300 may include fluidic connector 302, handle housing 304, actuation buttons 306, pressure transducer 308, pressure source 310, and processor housing 312. Fluidic connector 302 is configured to be coupled to implantable component 200, e.g., via reservoir 204, to permit fluidic communication with implantable component 200. Fluidic connector 302 may be a needle adapted to be inserted transcutaneously into implantable component 200, e.g., via insertion of the needle into a septum of reservoir 204. In one embodiment, reservoir 204 includes a conduit coupled to its internal cavity and configured to extend transcutaneously out of the patient, and fluidic connector 302 is a conduit configured to be coupled to the partially implanted conduit to permit fluid communication therebetween. In such an embodiment, repeated skin penetration by fluidic connector 302 may be limited. The partially implanted conduit may include a valve or cap configured to seal fluid within implantable component 200 when in a closed position.

Fluidic connector 302 is coupled to handle housing 304 which is configured to facilitate fluidic connector insertion. Handle housing 304 may include a grip sized to be held by a human hand and may house electronics, one or more valves, one or more pumps, one or more actuation buttons 306, and one or more pressure transducers 308 or, alternatively, one or more of those components may be housed in processor housing 312. Handle housing 304 also may be syringe-shaped and further include one or more plungers. Actuation buttons 306 are configured to be pressed to cause fluid from pressure source 310 to be injected into implantable component 200 via fluidic connector 302. For example, pressing a first actuation button 306 may cause a valve between pressure source 310 and fluidic connector 302 to open to permit fluid to flow out of fluidic connector 302 or may cause a pump to activate to move fluid in a first direction from pressure source 310 and out of fluidic connector 302. As another example, pressing a second actuation button 306 may cause one or more valves to open or close and cause the pump to activate to create a vacuum and move fluid in a second direction, opposite the first, e.g., from implantable component 200, through fluidic connector 302, and into a waste reservoir. While actuation buttons 306 are illustrated as buttons, the present disclosure is not limited thereto and the actuation mechanism may be embodied in, for example, a trigger(s), a touch screen, or the like. Pressure transducer 308 is disposed in fluid communication with fluidic connector 302 such that pressure transducer 308 may generate a signal indicative of pressure within implantable component 200 when fluidic connector 302 is inserted in implantable component 200. Pressure source 310 is a reservoir configured to hold fluid to be injected into implantable component 200 through fluidic connector 302 when fluidic connector 302 is in fluidic communication with implantable component 200. The fluid may be a liquid or gas, which may be pressurized or compressed, and pressure source 310 may be permanently integrated in external clinical controller component 300 or may be replaceable cartridges.

Handle housing 304 may be coupled, either wirelessly or using a cable such as cable 314, to processor housing 312. Processor housing 312 is configured to house processing electronics which may include signal filters and components for wave shaping. For example, the electronics may receive the signal indicative of pressure and process the signal for display and/or transmission to a computer. Processor housing 312 may include user interface 316 for receiving user input relating to adjustments to functioning of component 300 and/or display of measured parameters such as pressure within implantable component 200. As will be readily understood by one skilled in the art, while handle housing 304 and processor housing 312 are illustrated as two housings, the disclosure is not limited thereto and handle housing 304 and processor housing 312 may be integrated into one housing or separated into more than two housings. In embodiments where fluid is configured to travel between handle housing 304 and processor housing 312; such as when pressure source 310, a waste reservoir, and/or a pump is disposed in processor housing 312; cable 314 may include one or more lumens for fluid transfer or additional fluid cables may be used.

In FIG. 1, software-based monitoring system 400 is installed and runs on a conventional laptop computer, and is used by the patient's clinician to monitor functioning of implantable components 200. During patient visits, external clinical controller component 300 may be coupled, either wirelessly or using a cable such as cable 318, to the clinician's computer such that software-based monitoring system 400 may receive data indicative of working parameters of implantable device 200. Software-based monitoring system 400 may be non-transitory computer readable media configured to cause a graphical user interface to display information indicative of measured parameters within implantable component 200 based on signals received from sensors at implantable component 200 and/or external clinical controller component 300, and may also receive signals from external monitoring component 500 via the mobile device running mobile application 600. For example, the non-transitory computer readable media may cause the graphical user interface to display information indicative pressure within implantable component 200 based on a signal from pressure transducer 308. Monitoring system 400 also may be configured to upload and store data retrieved regarding implantable component 200 to a remote server for later access by the clinician.

External monitoring component 500 may include housing 502 and user interface 504. External monitoring component 500 permits a user; e.g., patient, clinician, caregiver; to monitor measured parameters within implantable component 200 at any time convenient for the patient. Housing 502 is configured to house electronics and may be shaped in any manner to permit handheld use such as a disc with rounded edges as illustrated. Such electronics may include an inductive coil and/or RF transceiver configured to communicate information in a bidirectional manner across a patient's skin to implantable component 200 and, optionally, to transmit power to electronics within implantable component 200. For example, in an embodiment where a pressure sensor is disposed within reservoir 204, external monitoring component 500 may include inductive communication circuitry configured to wirelessly activate the pressure sensor to cause the pressure sensor to sense a pressure within implantable component 200. The pressure sensor may transmit a pressure signal indicative of the sensed pressure to external monitoring component 500 via the inductive coil or a RF transceiver. The RF transceiver within housing 502 or an additional wireless transceiver within housing 502 may be configured for wireless communication; e.g., via WiFi, Bluetooth, cellular, or the like; with corresponding wireless communication circuitry in the mobile device running mobile application 600 and/or the computer running monitoring system 400. User interface 504 is configured to permit a user to provide user input to external monitoring component 500. User interface 504 may include a display and one or more buttons as illustrated, although the present disclosure is not limited thereto. A user may, for example, press a button to cause the inductive communication circuitry to transmit power to a sensor within implantable component 200. After receipt of one or more signals indicative of measured parameters from the sensor via communication circuitry, the display of user interface 504 may display the measured parameter. Alternatively, or additionally, external monitoring component 500 may transmit the one or more signals to mobile application 600.

Mobile application 600 is installed and runs on a conventional mobile device; e.g., smartphone, smart watch, tablet, laptop, or the like; and is used by the user to monitor functioning of internal components 200. External monitoring component 500 may be coupled, either wirelessly or using a cable, to the user's mobile device such that mobile application 600 receives data indicative of working parameters of implantable device 200. Mobile application 600 may be non-transitory computer readable media configured to cause a graphical user interface to display information indicative of measured parameters within implantable component 200 based on signals received from sensors at implantable component 200. For example, wireless communication circuitry within the mobile device; e.g., WiFi circuitry, Bluetooth circuitry, cellular circuitry or the like; may receive information indicative of pressure within implantable component 200 based on the pressure signal received at external monitoring component 500. User interface 602 of the mobile device may display the measured pressure, the status of implantable component 200, and/or an alert if a measured parameter is above a first predetermined threshold or below a second predetermined threshold. Such an alert may be transmitted to the clinician, e.g., via monitoring system 400, or may cause the mobile device to call the clinician or an emergency number for immediate patient assistance.

System 100 is configured to enhance monitoring of implantable component 200 to assist in confirming proper functioning of implantable component 200. For example, a clinician may determine an optimal internal pressure for implantable component 200 on a patient-by-patient basis. During patient visits, the clinician may confirm that the pressure within implantable component 200 is within a predetermined range around the optimal internal pressure using external clinical controller 300 and monitoring system 400. If not, the clinical may make adjustments to pressure by introducing or removing fluid using external clinical controller 300. The clinician may also remove fluid from within implantable component 200 using external clinical controller 300 after a predetermined time period; e.g., weekly, monthly, yearly, during each visit; and introduce new fluid using external clinical controller 300 to achieve the optimal internal pressure or an adjusted optimal internal pressure as treatment progresses.

System 100 is designed to restore compliance to the pulmonary system. Implantable component 200 is configured to reduce the pressure that the right ventricle must work against, thereby increasing cardiac output and slowing disease progression, and the remaining components of system 100 help ensure that implantable component is functioning suitably. Implantable component 200 also is configured to increase the diastolic pressure and slow the pulse wave such that the reflected waves do not contribute to afterload. It is expected that implantable component 200 will reduce the load on the heart and allow the heart to pump more blood using less energy; thereby preventing, delaying, or potentially reversing right heart failure.

Figure 2C:
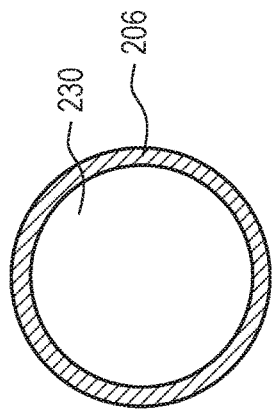
FIGS. 2C through 2E show cross-sectional views along line 2C in FIG. 2A for alternative conduits.
Figure 2D:
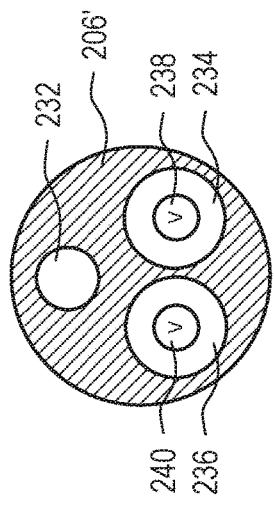
Figure 2E:
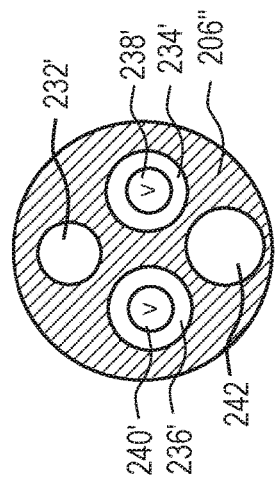
Figure 2A:
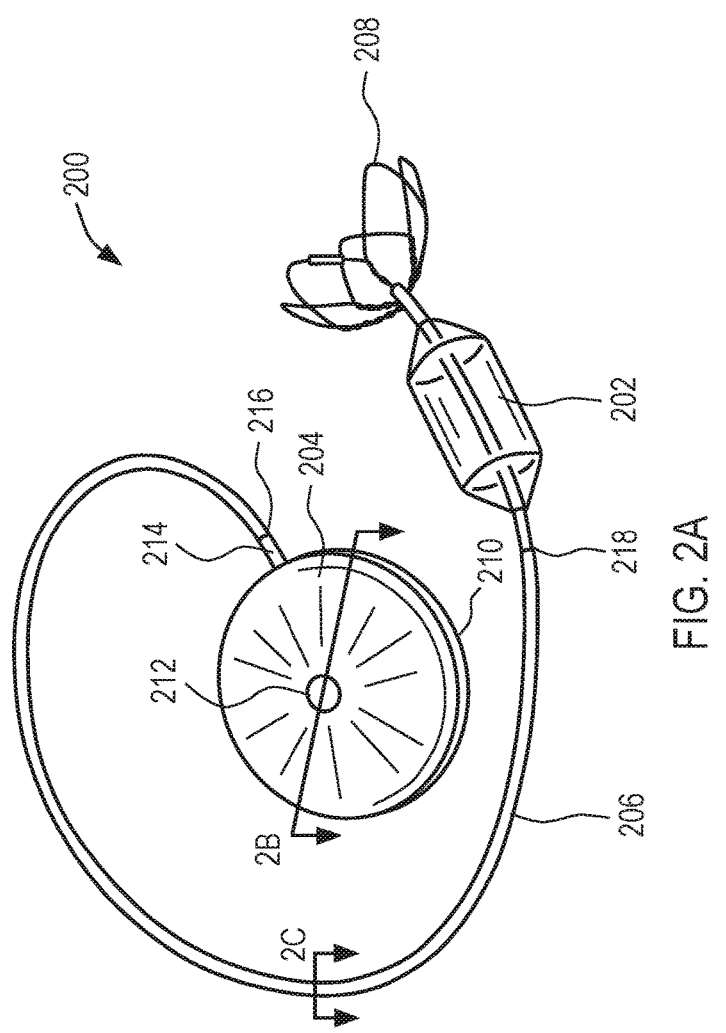
FIG. 2A shows an exemplary implantable component of the system of FIG. 1.

Referring now to FIG. 2A, an exemplary embodiment of implantable component 200 is described. Implantable component 200 includes compliant member 202, reservoir 204, and conduit 206. Compliant member 202 is adapted to be implanted in a body lumen, e.g., the pulmonary artery which includes the main pulmonary artery and the pulmonary artery branches. Compliant member 202 is preferably a compliant or semi-compliant balloon and may be formed from a polymer, an elastic material, e.g., rubber, and/or a flexible but inelastic material, e.g., metalized mylar. Compliant member 202 may have a single layer wall or multiple layers of multiple materials with one or more layers being formed of composite materials with reinforcing fibers. Compliant member 202 has a maximum diameter, a length, and a wall thickness. Preferably, compliant member 202 has a maximum diameter between about 1.5-3.5 cm, and preferably about 2.5 cm; a length between about 3-8 cm, and preferably about 4.5-5 cm; and a wall thickness between about 0.001-0.020 inches. Compliant member 202 preferably has a diameter in the fully expanded state that is less than the diameter of the pulmonary artery. For example, the diameter of compliant member 202 in the fully expanded state may be between about 20-90%, about 30-80%, about 40-75%, about 50-70%, about 55-70%, about 60-70%, or about 65% of the diameter of the pulmonary artery in the area at which compliant member 202 is implanted. Applicant has discovered that utilizing a compliant member sized such that the ratio of the inner diameter of the body lumen to the maximum balloon diameter is below a predetermined threshold; e.g., about 0.9, about 0.875, about 0.85, about 0.825, about 0.8, about 0.75, about 0.7, about 0.65, or about 0.6; maintains pressure upstream from the compliant member at a level substantially similar to pressure downstream from the compliant member; thereby regulating pressure drop across the compliant member during the cardiac cycle. Compliant member 202 is preferably sized with a maximum diameter that will not obstruct blood flow or increase resistance to flow in the pulmonary artery.

With each heartbeat, fluid within implantable component 200 moves towards or away from compliant member 202. By contracting and getting smaller in volume, compliant member 202 mimics the expansion of the vessel (increasing intravascular volume) that would naturally occur in a healthy person, making room for incoming blood. When the heart begins to relax, the pulmonary valve closes and the pressure in the main pulmonary artery begins to drop. As the pressure drops below the pressure level in reservoir 204, fluid flows from reservoir 204 to compliant member 202 such that the potential energy within compliant member 202 increases. During diastole, compliant member 202 preferably expands to about its full volume to increase pressure in the pulmonary artery to push additional blood through the lungs. Continuous expansion and contraction of compliant member 202 is expected to reduce peak systolic pressure and increase diastolic pressure, thereby reducing the load on the right ventricle and increasing heart efficiency.

Compliant member 202 may be secured within the body lumen via anchor 208. Anchor 208 may be coupled to compliant member 202, to conduit 206 proximal to compliant member 202, and/or to conduit 206 distal to compliant member 202 as illustrated. Preferably, anchor 208 is configured to expand from a contracted state, e.g., when compressed in a sheath, to an expanded state responsive to an event, e.g., exposure from the sheath or expansion of compliant member 202. In the expanded state, anchor 208 is sized to contact the inner wall of the body lumen or another anchor deployed within the body lumen as described in detail below.

Reservoir 204 is configured to receive and hold a fluid, e.g., liquid or gas, therein. Reservoir 204 includes housing 210, septum 212, and port 214. Housing 210 is hermetically sealed and may comprise titanium or other biocompatible material. Reservoir 204 is configured to be implanted subcutaneously in a suitable body cavity, e.g., within a subcutaneous space in a region near the right or left subclavian vein. Although any suitable shape may be used, in one exemplary embodiment, reservoir 204 has a flattened disk shape with rounded edges to reduce bodily irritation. The interior cavity of reservoir 204 is in fluidic communication with the interior cavity of compliant member 202, e.g., via one or more lumens of conduit 206, such that fluid may move between the cavities and/or pressure may equalize between the cavities. Preferably, the interior cavity of reservoir 204 has a volume of about 40-250 ml, about 40-150 ml, about 40-100 ml, about 40-70 ml, or about 60 ml.

Septum 212 is structured and operable to allow the addition of fluid to or the removal of fluid from reservoir 204. Septum 212 is preferably implanted underneath the patient's skin to permit transcutaneous needle access to the interior cavity of reservoir 204 through septum 212. Septum 212 is configured to permit repeated needle penetrations while maintaining a gas-tight seal and may be formed from any suitable material or materials that reduces diffusion of fluid from the internal cavity of reservoir 204. Radiopaque, magnetic, acoustic, or other markers may also be incorporated into or attached to septum 204 to allow for locating, viewing or tracking of septum 204 with a suitable imaging or sensing system.

Port 214 of reservoir 204 is configured to permit fluidic communication between conduit 206 and the interior cavity of reservoir 204. Port 214 may include a suitable structure to permit coupling between conduit 206 and reservoir 204 such as a nipple (as illustrated), threads, ribs, or the like.

Figure 2B:
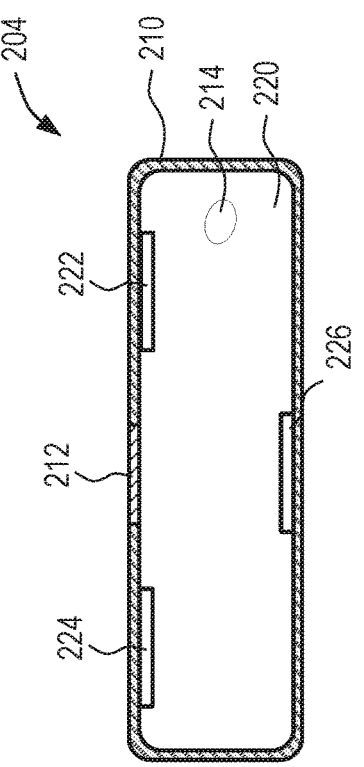
FIG. 2B shows a cross-sectional view along line 2B in FIG. 2A of an exemplary reservoir.

Referring now to FIG. 2B, a cross-sectional view of reservoir 204 along line 2B in FIG. 2A is shown. Interior cavity 220 of reservoir 204 may have sensor 222, sensor 224, and getter 226. Sensors 222, 224 are configured to sense one or more parameters of implantable component 200 such as pressure and/or volume within reservoir 204. Such parameters may be used to assist in removing fluid or introducing fluid to achieve the optimal internal pressure or to confirm proper functioning of implantable component 200. Additional parameters that may be sensed within reservoir 204 include temperature, humidity, fluid flow rate, gas or liquid concentration such as $CO_2$ concentration, and pH. Sensors 222 and 224 may include an inductive coil and may be configured to be powered by an external inductive coil, e.g., coil within external monitoring component 500. In such an embodiment, sensors 222, 224 may remain off or in a standby mode until receipt of power; after which sensors 222, 224 sense one or more parameters and transmit one or more signals indicative of the sensed parameters externally, e.g., to external monitoring component 500, via respective inductive coils. In a preferred embodiment, sensor 222 is a pressure sensor configured to measure pressure within reservoir 204. Measured pressure may be displayed and analyzed externally.

Getter 226 is configured to absorb moisture within reservoir 204. Unwanted moisture from within the body may enter implantable component 200 after implantation. Preferably when the fluid is a gas, getter is configured to absorb liquids within reservoir 204. Getter 226 may be removed, e.g., via fluidic connector 302, and replaced with another getter, e.g., via fluidic connector 302, after a period of time.

Referring back to FIG. 2A, conduit 206 is configured to couple compliant member 202 to reservoir 204. Conduit 206 includes proximal region 216 and distal region 218. In the illustrated embodiment, conduit 206 is coupled to port 214 of reservoir 204 at proximal region 216 and coupled compliant member 202 at distal region 218. Preferably, conduit 206 has a suitable length to extend from reservoir 204 in the subcutaneous space, through the subclavian vein, and past the pulmonary valve to compliant member 202 implanted within the pulmonary artery. Preferably, conduit 206 extends through and past compliant member 202 a predetermined distance and includes one or more ports in the portion of conduit 206 within compliant member 202 to permit fluid to be introduced from conduit 206 into the interior space of compliant member 202. In one embodiment, conduit 206 has a length between about 20-70 cm, about 30-70 cm, about 40-70 cm, about 50-60 cm, or about 55 cm. The diameter of conduit 206 is preferably about 3-5 mm or about 4 mm at distal region and may be variable along the length of conduit 206 up to a predetermined maximum diameter, e.g., about 15 mm. Preferably, conduit 206 has a wall thickness between about 0.005 to 0.020 inches.

Referring now to FIGS. 2C, 2D, and 2E, cross-sectional views of alternative conduits along line 2C in FIG. 2A are shown wherein the number of lumens within the conduits vary. In FIG. 2C, conduit 206 has lumen 230. Lumen 230 is configured to permit fluid to move back and forth between compliant member 202 and reservoir 204. Lumen 230 preferably extends from proximal region 216 to a port within compliant member 202. Conduit 206 also may include a second lumen (not illustrated) sized to permit a guidewire and/or a balloon retrieval device to be advanced therethrough that preferably extends from the proximal end of conduit 206 out the distal end of conduit 206 past compliant member 202. Referring to FIG. 2D, conduit 206' is constructed similarly to conduit 206 of FIG. 2C, wherein like components are identified by like-primed reference numbers. As will be observed by comparing FIGS. 2C and 2D, conduit 206' includes three lumens; guidewire lumen 232, inflow lumen 234, and outflow lumen 236. Guidewire lumen 232 is sized to permit a guidewire and/or a balloon retrieval device to be advanced therethrough and preferably extends from the proximal end of conduit 206 out the distal end of conduit 206 past compliant member 202. Inflow lumen 234 is configured to permit fluid to move only from reservoir 204 to compliant member 202, e.g., using one-way valve 238. Inflow lumen 234 preferably extends from proximal region 216 to a port within compliant member 202. Outflow lumen 236 is configured to permit fluid to move only from compliant member 202 to reservoir 204, e.g., using one-way valve 240 disposed in an opposite direction to valve 238. Outflow lumen 236 preferably extends from proximal region 216 to a port within compliant member 202. Referring to FIG. 2E, conduit 206" is constructed similarly to conduit 206' of FIG. 2D, wherein like components are identified by like-primed reference numbers. As will be observed by comparing FIGS. 2D and 2E, conduit 206" includes a fourth lumen: lumen 242. Lumen 242 is configured to permit a balloon retrieval device to be advanced therethrough and has a diameter larger than guidewire lumen 232'.

Figure 2G:
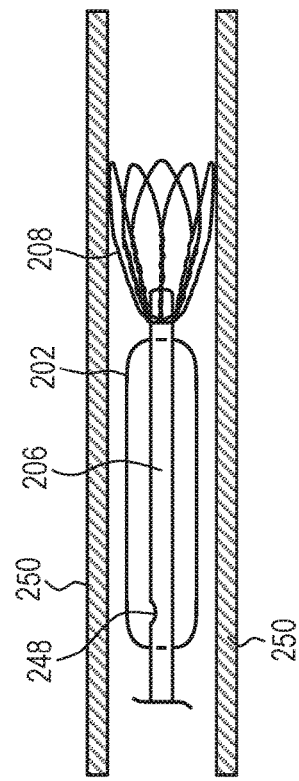
FIGS. 2F and 2G show an exemplary anchor of the implantable component of FIG. 2A, where anchor is in an expanded state in FIG. 2F and contracted within a sheath in FIG. 2G.
Figure 2F:
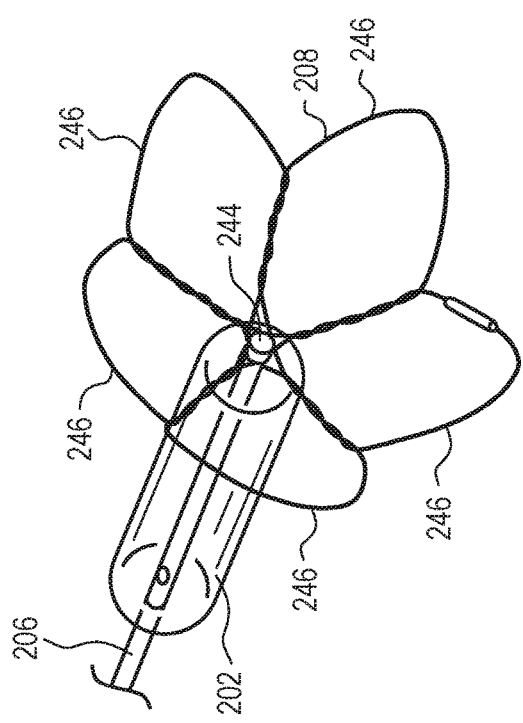

Referring now to FIG. 2F, a front view of anchor 208 of implantable component 200 in FIG. 2A is provided. Anchor 208 is coupled to conduit 206 between the distal end of compliant member 202 and distal end 244 of conduit 206. Anchor 208 may comprise shape memory material, e.g., nitinol, and is preferably configured to self-expand when exposed from a sheath. Illustratively, anchor 208 includes five petals 246 although more or fewer petals may be used. In FIG. 2F, anchor 208 is shown in an expanded state. In the expanded state, the distal regions of petals 246 are sized to contact the inner wall of the body lumen, e.g., pulmonary artery, or another anchor deployed within the body lumen.

In FIG. 2G, the distal region of implantable component 200 is shown in a contracted state. Preferably, compliant member 202 is in a contracted, deflated state when disposed within sheath 250. After deployment, compliant member 202 may be expanded by introduction of fluid from reservoir 204 through port 248. When compressed within sheath 250, anchor 208 bends distally away from compliant member 202. Anchor 208 is configured to expand to the expanded state when the distal end of sheath 250 is retracted proximally past anchor 208 or when anchor 208 is pushed distally out of the distal end of sheath 250. After deployment of anchor 208 and compliant member 202 past the distal end of sheath 250, sheath 250 may be removed from the patient or sheath 250 may be permanently implanted at a position such that the distal end of sheath 250 does not interfere with expansion of compliant member 202 or anchor 208 and the proximal end of sheath 250 does not interfere with coupling the proximal end of conduit 206 to reservoir 204. After deployment, sheath 250, or another similar sheath, may be advanced distally, or conduit 206 pulled proximally, such that compliant member 202 and anchor 208 enter the lumen of sheath 250 at its distal end to return anchor 208 to the contracted state. Conduit 206 and compliant member 202, including anchor 208, then may be retrieved from sheath 250, e.g., by detaching the proximal end of conduit 206 from reservoir 204 and pulling the proximal end of conduit 206 proximally out the proximal end of sheath 250. If desired, a replacement conduit and/or replacement compliant member may be introduced into the patient through sheath 250 and then attached to reservoir 204 at the proximal end of the replacement conduit.

Figure 2I:
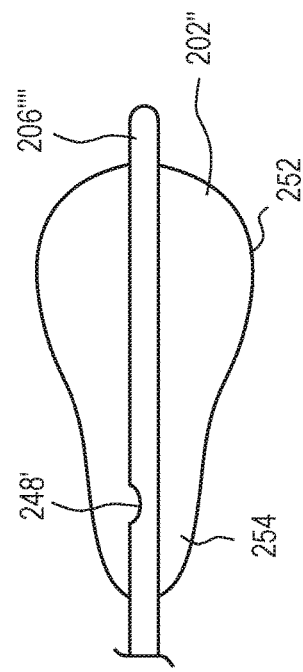
FIG. 2I shows an alternative balloon for use in the implantable component wherein the balloon has a tapered shape.
Figure 2H:
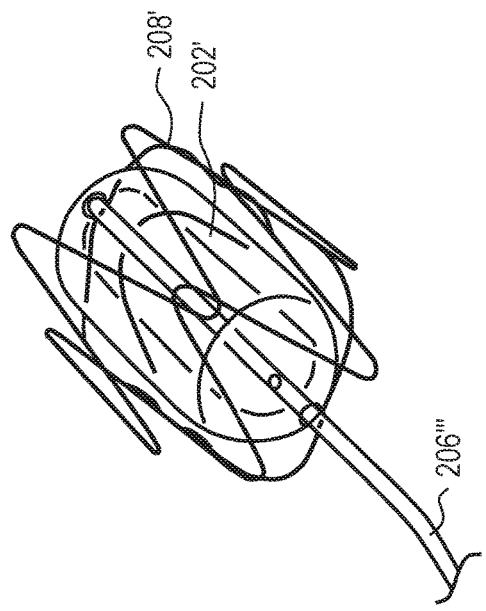
FIG. 2H shows an alternative anchor for use with the implantable component.

Referring to FIG. 2H, compliant member 202' and conduit 206''' are constructed similarly to compliant member 202 and conduit 206 of FIG. 2F, wherein like components are identified by like-primed reference numbers. As will be observed by comparing FIGS. 2F and 2H, anchor 208' is shaped to surround compliant member 202' rather than disposed distally to the compliant member. Anchor 208' is coupled to conduit 206''' distal to compliant member 202' and coupled to conduit 206''' proximal to compliant member 202'. Anchor 208' is configured to radially expand from a contracted state, e.g., when compressed in a sheath, to an expanded state responsive to an event, e.g., exposure from the sheath or expansion of compliant member 202'. In the expanded state, the outer surface of anchor 208' is sized to contact the inner wall of the body lumen. In one embodiment, the outer portion of anchor 208' has a length substantially similar to the length of compliant member 202'.

Referring to FIG. 2I, conduit 206'''' is constructed similarly to conduit 206 of FIG. 2F, wherein like components are identified by like-primed reference numbers. As will be observed by comparing FIGS. 2F and 2I, anchor 208 is not shown for simplicity and compliant member 202" has a tapered shape along a substantial portion of its length rather than a cylindrical shape. Compliant member 202", shown in the expanded state, has large diameter end 252, small diameter end 254, and a sloping portion therebetween. Preferably, compliant member 202" is implanted in the body lumen such that blood flows from small diameter end 254 towards large diameter end 252. The tapered shape of compliant member 202" is configured to reduce billowing of compliant member 202" caused by ejection of blood during systole. As will be understood by one of ordinary skill, while compliant member 202 has a cylindrical shape and compliant member 202" has a tapered shape, the present disclosure is not limited thereto and additional balloon shapes are contemplated herein.

Referring to FIG. 2J, compliant member 202''' and conduit 206''''' are constructed similarly to compliant member 202 and conduit 206 of FIG. 2F, wherein like components are identified by like-primed reference numbers. As will be observed by comparing FIGS. 2F and 2J, anchor 208''' is shaped in a rolled manner and includes arms 260 and 262. In FIG. 2J, anchor 208''' is contracted within sheath 250' and introduced into the pulmonary artery PA for implantation. In the contracted state, arms 260 and 262 roll radially inward toward conduit 206''''. When exposed from sheath 250', arms expand radially outward such that a distal region of arms 260 and 262 contact the inner wall of the pulmonary artery as shown in FIG. 2K. Arms 260 and 262 may be constructed with a shape memory material and may self-expand to resemble an "S" shape in the expanded state. In one embodiment, arms 260 and 262 are constructed similarly to the anchors of U.S. Pat. No. 4,666,445 to Tillay, the entire contents of which are incorporated herein by reference. Arms 260 and 262 may be coupled to conduit 206'''' distal to compliant member 202''' as illustrated or proximal to compliant member 202'''. Alternatively, additional arms may be used, including two arms disposed distal to the compliant member and two arms disposed proximal to the compliant member. In FIG. 2K, compliant member 202''' is shown in an expanded state.

FIG. 2L is a side view of the components of FIG. 2K where arms 260 and 262 are in the expanded state. Arms 260 and 262 each has a width large enough to suitably anchor compliant member 202''' stably within the pulmonary artery PA.

Alternatively, arms 260' and 262' may be wire-like and have a relatively thin width. In such an embodiment, arms 260' and 262' may be anchored within a previously deployed anchor, e.g., anchor 270 shown in FIGS. 2M and 2N. Anchor 270 illustratively includes protrusions 272 and 274 and groove 276 disposed between protrusions 272 and 274. In one embodiment, protrusions 272 and 274 have an annular shape. Anchor 270 is configured to radially expand from a contracted state, e.g., when compressed in a sheath, to an expanded state responsive to an event, e.g., exposure from the sheath or expansion of compliant member 202''''. In the expanded state, the outer surface of anchor 270 is sized to contact the inner wall of the body lumen, e.g., the pulmonary artery PA as shown in FIG. 2M. After deployment of anchor 270, the anchor coupled to the conduit may be anchored to anchor 270. For example, compliant member 202'''' may be advanced in a sheath when arms 260' and 262' are in the contracted state. When arms 260' and 262' are aligned within groove 276, the sheath is pulled proximally such that arms 260' and 262' expand radially outward and contact groove 276 as shown in FIG. 2N. Protrusions 272 and 274 are configured to maintain arms 260' and 262' within groove 276. The distal end of the sheath, arms 260' and 262', and/or protrusions 272 and 274 may include radiopaque markers to permit visualization during delivery to assist in proper alignment. In one embodiment, arms 260, 260', 262, and 262' are configured to roll back to the contracted state when the conduit is rotated to facilitate insertion of the arms within the sheath for conduit and compliant member removal. In such an embodiment, arms 260, 260', 262, and 262' are configured to radially expand when the conduit is rotated in a first direction, e.g., clockwise, and to radially contract when the conduit is rotated in a second direction, opposite the first direction, e.g., counterclockwise.

Implantable component 200 may be used together with drugs, such as anticoagulants, to reduce the risk of pulmonary emboli. Advantageously, implantable component 200 is expected to provide one or more of the following patient benefits through increased pulmonary vascular compliance: (i) decreased stress on the heart—as blood is ejected into the main pulmonary artery, compliant member 202 is compressed, mimicking how a healthy pulmonary artery expands to make room for incoming blood, thereby reducing systolic pressure; (ii) increased cardiac output—decreased load on the heart caused by repeated expansion and contraction of compliant member 202 allows more blood to flow to the lungs; (iii) decreased workload on the heart—repeated expansion and contraction of compliant member 202 reduces the mechanical work required to pump blood thereby redistributing work load in the right ventricle to reduce or prevent right ventricular remodeling, e.g., conversion of elastin to collagen; (iv) slowed progression of PH—repeated expansion and contraction of compliant member 202 reduces the cyclic strain on the small pulmonary arteries to slow the progression of vascular thickening and/or remodeling caused by PH; (v) immediate effectiveness—in contrast to drug therapy, implantable component 200 is configured to decrease the workload on the heart immediately upon implantation and may be utilized in emergency situations; and (vi) effective even in advanced cases of PAH.

Implantable component 200 may be implanted within a patient such that compliant member 202 is positioned within the pulmonary artery distal to the pulmonary valve, reservoir 204 is positioned within a subcutaneous space, and conduit 206 extends from reservoir 204 through the subclavian vein to, and potentially past, compliant member 202. For implantation, an incision may be made in the subclavicular skin, e.g., under the collarbone, and a pocket formed in the subcutaneous space. Then, an incision may be made in the subclavian vein. Upon forming the first and second incisions, a guidewire may be inserted into the subclavian vein and through the venous system such that the distal end of the guidewire is positioned in the pulmonary artery distal to the pulmonary valve. Using fluoroscopy, acoustic, anatomic, or CT guidance, throughout the procedure, sheath 250 then may be delivered over the guidewire. Next, compliant member 202 coupled to conduit 206 may be advanced through sheath 250 until compliant member 202 is extracted out the distal end of sheath 250. Alternatively, compliant member 202 and conduit 206 may be pre-loaded within sheath 250 external to the patient's body and advanced over the guidewire together. In such a configuration, sheath 250 may be retracted to expose compliant member 202 at the desired position within the pulmonary artery or compliant member may be advanced distally out of the distal end of sheath 250 at the desired position within the pulmonary artery. With compliant member 202 positioned in the desired resting position, e.g., via anchor 208, sheath 250 and the guidewire may be removed. Alternatively, sheath 250 may remain implanted to facilitate removal of conduit 206 and compliant member 202 and introduction of replacement conduits and compliant members. Reservoir 204 may then be coupled to conduit 206 and placed in the subcutaneous pocket and the incisions closed. Fluid may be injected into the septum of reservoir 204 until a desired internal pressure is reached before or after the incisions are closed.

Figure 3:
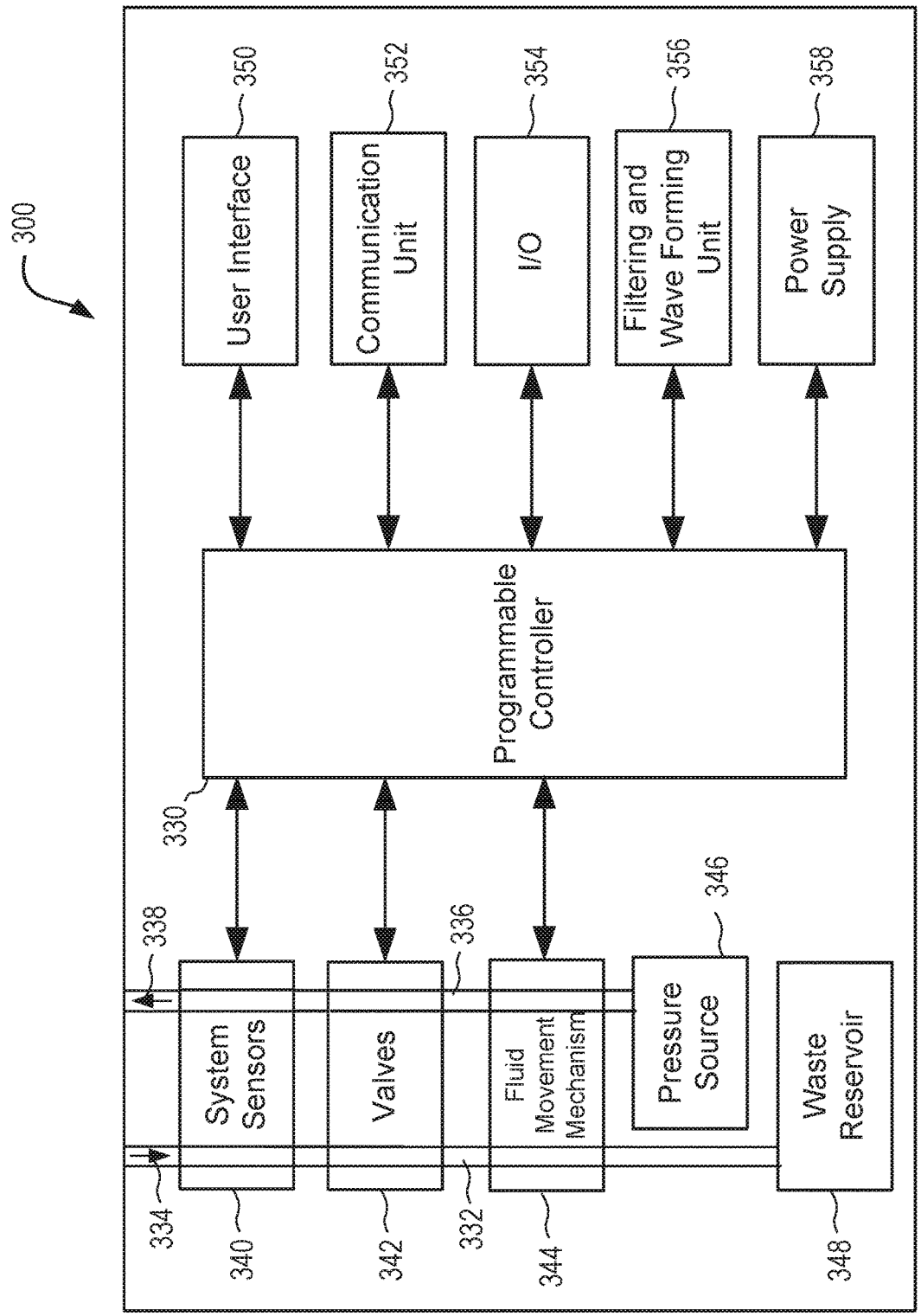
FIG. 3 shows a generalized block diagram of an exemplary external clinical controller component of the system of FIG. 1.

Referring to FIG. 3, a generalized schematic diagram of the internal functional components of external clinical controller component 300 is now described. External clinical controller component 300 may include programmable controller 330, extraction lumen 332 where fluid moves in direction 334, injection lumen 336 where fluid moves in direction 338, system sensors 340, valves 342, fluid movement mechanism 344, pressure source 346, waste reservoir 348, user interface 350, communications unit 352, input and output circuitry (I/O) 354, filtering and wave forming unit 356, and power supply 358.

Programmable controller 330 is electrically coupled to, and configured to control, the internal functional components of external clinical controller component 300. Controller 330 may comprise one or more commercially available microcontroller units that may include a programmable microprocessor, volatile memory, nonvolatile memory such as EEPROM for storing programming, and nonvolatile storage, e.g., Flash memory, for storing firmware and a log of system operational parameters and patient data. The memory of controller 330 stores program instructions that, when executed by the processor of controller 330, cause the processor and the functional components of external clinical controller component 300 to provide the functionality ascribed to them herein. Controller 330 is configured to be programmable such that programming data is stored in the memory of controller 330 and may be adjusted using monitoring system 400. As will be readily understood to one skilled in the art, while FIG. 3 is illustrated to show one programmable controller, multiple programmable controllers may be utilized. For example, in an embodiment where the handle housing and processor housing are separate, each housing may include at least one programmable controller.

Extraction lumen 332 is configured to permit fluid to move therethrough in direction 334, e.g., away from implantable component 200, and preferably extends from the distal end of fluidic connector 302 to waste reservoir 348. Extraction lumen 332 may be coupled to one or more sensors of system sensors 340, one or more valves of valves 342, fluid movement mechanism 344, and/or waste reservoir 348.

Injection lumen 336 is configured to permit fluid to move therethrough in direction 338, e.g., towards implantable component 200, and preferably extends from the distal end of fluidic connector 302 to pressure source 346. Injection lumen 336 may be coupled to one or more sensors of system sensors 340, one or more valves of valves 342, fluid movement mechanism 344, and/or pressure source 346. As will be readily understood by one skilled in the art, while FIG. 3 shows extraction lumen 332 and injection lumen 336 as separate, they may be integrated into a common lumen.

System sensors 340 are configured to sense one or more parameters of implantable component 200 such as pressure and/or volume within reservoir 204. System sensors 340 may generate one or more signals indicative of the sensed parameter(s) for processing and/or transmission to monitoring system 400. In one embodiment, such sensors are configured to sense the parameters when fluidic connector 302 is inserted into reservoir 204 through septum 212. Such parameters may be used to assist in removing fluid or introducing fluid to achieve an optimal internal pressure within implantable component 200 or to confirm proper functioning of implantable component 200. Parameters of implantable component 200 that may be sensed by system sensors 340 also may include temperature, humidity, fluid flow rate, volume of injected fluid, volume of extracted fluid, gas or liquid concentration such as $CO_2$ concentration, and pH. System sensors 340 may include pressure transducer 308 and are preferably disposed in fluidic communication with the fluidic connector lumen(s), e.g., extraction lumen 332 and/or injection lumen 336. In a preferred embodiment, when fluidic connector 302 is inserted into reservoir 204, the pressure transducer is configured to measure pressure within reservoir 204.

Valves 342 are configured to permit fluid to flow therethrough when opened and to prevent fluid flow therethrough when closed. In one embodiment, a one-way valve is disposed in extraction conduit 332 and configured to permit fluid to flow in direction 334 when opened. In addition, or alternatively, a one-way valve may be disposed in injection conduit 336 and configured to permit fluid to flow in direction 338 when opened. Valves 342 may be opened in response to user input received at user interface 350. For example, pressing a first actuation button of user interface 350 may cause a valve in injection lumen 336 to open to permit fluid to flow out of fluidic connector 302. As another example, pressing a second actuation button of user interface 350 may cause a valve in extraction lumen 334 to open and, optionally, cause fluid movement mechanism 344 to activate to create a vacuum and move fluid in direction 334.

Fluid movement mechanism 344 may be any suitable mechanism for moving fluid in a forward direction and a reverse direction. For example, fluid movement mechanism 344 may be a bidirectional pump, a unidirectional pump, two unidirectional pumps configured to pump fluid in opposite directions, a plunger, two plungers configured to move fluid in opposite directions, or the like. Fluid movement mechanism 344 may be activated responsive to user input received at user interface 350 to move fluid from pressure source 346 and out the distal end of fluidic connector 302. In one embodiment, user input received at user interface 350 causes a pump to move fluid in direction 338, e.g., towards and into implantable component 200. In another embodiment, a clinician presses a plunger to move fluid from pressure source 346 in direction 338, e.g., towards and into implantable component 200. In an embodiment where fluid within pressure source 346 is pressurized, fluid movement mechanism 344 need not necessarily be used to move fluid. Fluid movement mechanism 344 also may be activated responsive to user input to move fluid in an opposite direction from implantable component 200, into the distal end of fluidic connector 302, and into waste reservoir 348. In one embodiment, user input received at user interface 350 causes a pump to move fluid in direction 334, e.g., out of and away from implantable component 200. In another embodiment, a clinician pulls a plunger to move fluid from within implantable component 200 in direction 334, e.g., out of and away from implantable component 200.

Pressure source 346 is a reservoir configured to hold fluid to be injected into implantable component 200 through fluidic connector 302 when fluidic connector 302 is in fluidic communication with implantable component 200, e.g., by piercing the septum of reservoir 204. Pressure source 346 may correspond to pressure source 310 of FIG. 1. The fluid is preferably a biocompatible gas or biocompatible liquid and may include carbon dioxide ($CO_2$), air, oxygen, nitrogen, saline, water, or the like. The fluid may be selected to reduce the risk of diffusion through the outer walls of compliant member 202, reservoir 204, and/or conduit 206. The fluid may be pressurized or compressed and pressure source 346 may be refillable and permanently integrated in external clinical controller component 300 or may be replaceable cartridges, e.g., $CO_2$ cartridges.

Waste reservoir 348 is configured to hold fluid extracted from within implantable component 200 through fluidic connector 302 when fluidic connector 302 is in fluidic communication with implantable component 200, e.g., by piercing the septum of reservoir 204. For example, waste reservoir 348 may hold moisture that had accumulated within implantable component 200 and/or getter 226 that had absorbed moisture in reservoir 204.

User interface 350 is configured to receive user input and, optionally, to display information to the user. User interface 350 may include buttons for receiving user input, such as actuation buttons 306 or buttons of user interface 316, and a display for displaying information to the clinician, e.g., display of user interface 316 in FIG. 1. As will be readily apparent to one skilled in the art, user interface 350 is not limited thereto and may use one or more of a trigger, a plunger, a touch screen, a keypad, a microphone, a speaker, a trackball, or the like.

Communication unit 352 is configured to transmit information, such as signals indicative of sensed parameters and the like, to a remote location such as a computer running monitoring system 400. Communication unit 352 may include circuitry; e.g., WiFi, Bluetooth, and/or cellular chipsets; configured for wireless communication over a network such as the Internet, a local network, or a telephone network using techniques known in the art.

Input and output circuitry (I/O) 354 may include ports for data communication such as wired communication with a computer and/or ports for receiving removable memory, e.g., SD card, upon which program instructions or data related to external clinical controller component 300 use may be stored. In one embodiment, I/O 354 comprises ports, and corresponding circuitry, for accepting cables 314 and 318 such that external clinical controller component 300 is electrically coupled to a computer running software-based monitoring system 400.

Filtering and wave forming unit 356 is configured to receive signals indicative of sensed parameters, e.g., from system sensors 340, and to process the signals. For example, filtering and wave forming unit 356 may include one or more filters configured to filter noise from the signals. Filtering and wave forming unit 356 also may include wave shaping processing circuitry known in the art for processing a signal for display of the measured parameter as a wave. For example, filtering and wave forming unit 356 may process a signal indicative of real-time sensed pressure within implantable component 200 such that a real-time pressure wave may be displayed on user interface 350 and/or on the display of the computer running monitoring system 400.

Power supply 358 powers the electrical components of external clinical controller component 300, and may comprise a primary cell or battery, a secondary (rechargeable) cell or battery or a combination of both. Alternatively, power supply 358 may be a port to allow external clinical controller component 300 to be plugged into a conventional wall socket for powering components. In one embodiment, power supply 358 comprises one or more ports and one or more cables that enable external clinical controller component 300 to be powered from the computer, e.g., via cables 314 and 318, running software-based monitoring system 400.

Figure 4:
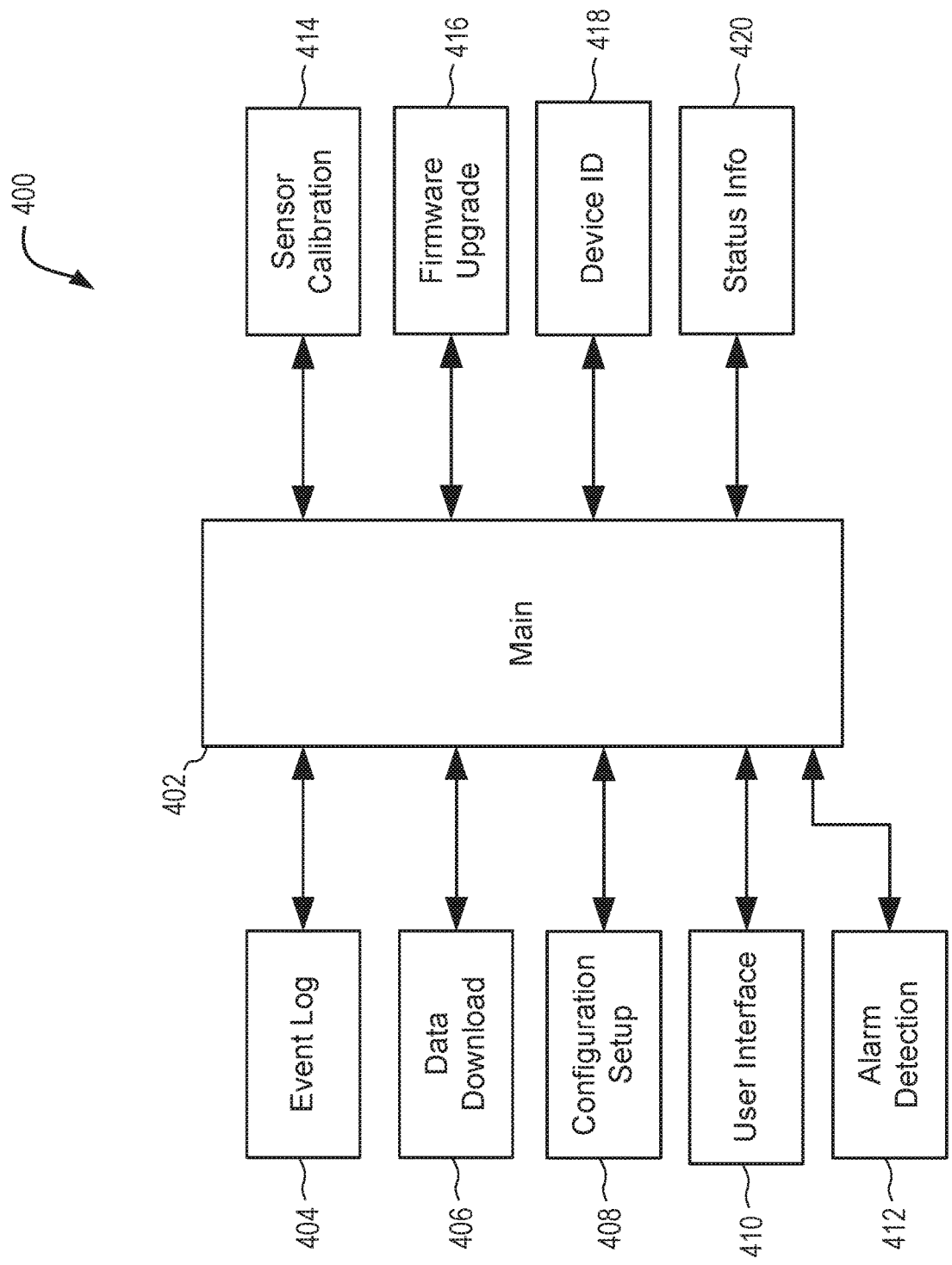
FIG. 4 is a block diagram of the functional components of an exemplary software-based monitoring system of the system of FIG. 1.

Referring now to FIG. 4, the software implementing monitoring system 400 is now described. The software of monitoring system 400 comprises a number of functional blocks, schematically depicted in FIG. 4, including main block 402, event logging block 404, data download block 406, configuration setup block 408, user interface block 410, alarm detection block 412, sensor calibration block 414, firmware upgrade block 416, device identifier block 418, and status information block 420. The software preferably is written in C++ and employs an object oriented format. In one preferred embodiment, the software is configured to run on top of a Microsoft Windows™ (a registered trademark of Microsoft Corporation, Redmond, Wash.) or Unix-based operating system, such as are conventionally employed on desktop and laptop computers. The computer running monitoring system 400 preferably includes a data port, e.g., USB port or comparable wireless connection, that permits external clinical controller component 300, external monitoring component 500, and/or the mobile device running mobile application 600 to be coupled thereto. Alternatively, or additionally, the computer may include wireless circuitry; e.g., conforming to the IEEE 802.11 standards, the 3G, 4G, LTE, or other cellular standards, and/or Bluetooth standards; thereby enabling external clinical controller component 300, external monitoring component 500, and/or the mobile device running mobile application 600 to communicate wirelessly with the computer running monitoring system 400.

Main block 402 preferably includes a main software routine that executes on the clinician's computer, and controls overall operation of the other functional blocks. Main block 402 enables the clinician to download event data and alarm information stored on external clinical controller component 300, external monitoring component 500, and/or the mobile device running mobile application 600 to his office computer, and also permits monitoring system 400 to receive signals indicative of sensed parameters from external clinical controller component 300, external monitoring component 500, and/or the mobile device running mobile application 600. Main block 402 further is configured execute routines to calculate parameters based on sensed parameters. For example, main block 402 is configured to execute a routine to calculate volume within implantable component 200 (e.g., compliant member 202, reservoir 204) using signals indicative of pressure sensed at implantable component 200 and known equations, such as Boyle's law. Other parameters may be calculated using sensed parameters such as pulmonary arterial compliance (PAC), added PAC, native PAC, mean pressure, systolic pressure, diastolic pressure, fluid diffusion rate, liquid penetration rate, compliant member collapse percentage, compliant member expanded volume, compliant member contracted volume, and compliant member total volume. Main block 402 further is configured execute routines to calculate data for display based on input received at User Interface block 410. For example, a clinician may enter implantable component 200 implantation date, implantable component 200 activation date, and time to next patient visit and routines are run to determine time since activation based on the activation date, time to recommended replacement based on the implantation and/or activation date, and the time to next patient visit. Main block 402 also enables the clinician to upload firmware updates and configuration data to external clinical controller component 300, external monitoring component 500, and/or the mobile device running mobile application 600.

Event Log block 404 is a record of operational data downloaded from external clinical controller component 300, external monitoring component 500, and/or the mobile device running mobile application 600, and may include, for example, measurement times, real-time sensed parameters, parameters previously sensed, sensor data, battery current, battery voltage, battery status, and the like. The event log also may include the occurrence of events, such as alarms or other abnormal conditions. Event Log block 404 may further include a record of data inputted at User Interface block 410 such as patient information, implantable component 200 implantation date, implantable component 200 activation date, and time to next patient visit.

Data Download block 406 is a routine that commands external monitoring component 500 and/or the mobile device running mobile application 600 to transfer data to monitoring system 400 for download after external clinical controller component 300 is coupled to the computer running monitoring system 400. Data Download block 406 may initiate, either automatically or at the instigation of the clinician via user interface block 410, downloading of data stored in the event log.

Configuration Setup block 408 is a routine that configures the parameters stored within external clinical controller component 300, external monitoring component 500, and/or the mobile device running mobile application 600 that control operation of the respective component/application. The parameters may determine, e.g., how long since a user sensed parameters within implantable component 200 and, if past a predetermined threshold, may alert the user. Such interval timing parameters may be reconfigured by block 408. Interval timing settings transmitted to external clinical controller component 300, external monitoring component 500, and/or the mobile device running mobile application 600 from monitoring system 400 also may determine when and how often event data is written to the memory in the respective component/application.

User interface block 410 handles receipt of user input at the computer running monitoring system 400 and display of information retrieved from external clinical controller component 300, external monitoring component 500, and/or the mobile device running mobile application 600, and data download block 406, and presents that information in an intuitive, easily understood format for clinician review such as numbers, wave forms, text, a plot, a chart, a graph, or the like. Such information may include status of external clinical controller component 300, status of external monitoring component 500, status of mobile application 600, patient information, implant timing information, time to implant replacement, measurement times, real-time sensed parameters, parameters previously sensed, parameters calculated using sensed parameters, sensor data, battery current, battery voltage, battery status, and the like.

Alarm detection block 412 may include a routine for evaluating the data retrieved from external clinical controller component 300, external monitoring component 500, and/or the mobile device running mobile application 600 and flagging abnormal conditions for the clinician's attention. For example, alarm detection block 412 may flag when a parameter sensed by system sensors 340, or sensors 222, 224, is above a first predetermined threshold or below a second predetermined threshold.

Sensor calibration block 414 may include a routines for testing or measuring drift, of system sensors 340 or sensors 222, 224, e.g., due to aging or change in humidity. Block 414 may then compute offset values for correcting measured data from the sensors, and transmit that information to sensors 222, 224 or external clinical controller component 300 for storage in the nonvolatile memory of controller 330.

Firmware upgrade block 416 may comprise a routine for checking the version numbers of the controller firmware installed on external clinical controller component 300, external monitoring component 500, and/or the mobile device running mobile application 600, and identify whether upgraded firmware exists. If so, the routine may notify the clinician and permit the clinician to download revised firmware to external clinical controller component 300, external monitoring component 500, and/or the mobile device running mobile application 600, in nonvolatile memory.

Device identifier block 418 consists of a unique identifier for implantable component 200 that is stored in an RFID coupled to implantable component 200 and a routine for reading that data when monitoring system 400 is coupled to an RFID reader, e.g., in external clinical controller component 300. The device identifier also may be used by implantable component 200 to confirm that wireless communications received from external monitoring component 500 are intended for that specific device. Likewise, this information is employed by external monitoring component 500 to determine whether a received message was generated by implantable component 200 associated with that system. Alternatively, the device identifier may be inputted at User Interface block 410 and stored in memory of the computer running monitoring system 400.

Status information block 420 comprises a routine for interrogating external clinical controller component 300, external monitoring component 500, and/or the mobile device running mobile application 600 to retrieve current status data from external clinical controller component 300, external monitoring component 500, and/or the mobile device running mobile application 600, respectively. Such information may include, for example, battery status, version control information for the firmware and hardware currently in use, and sensor data.

Figure 5:
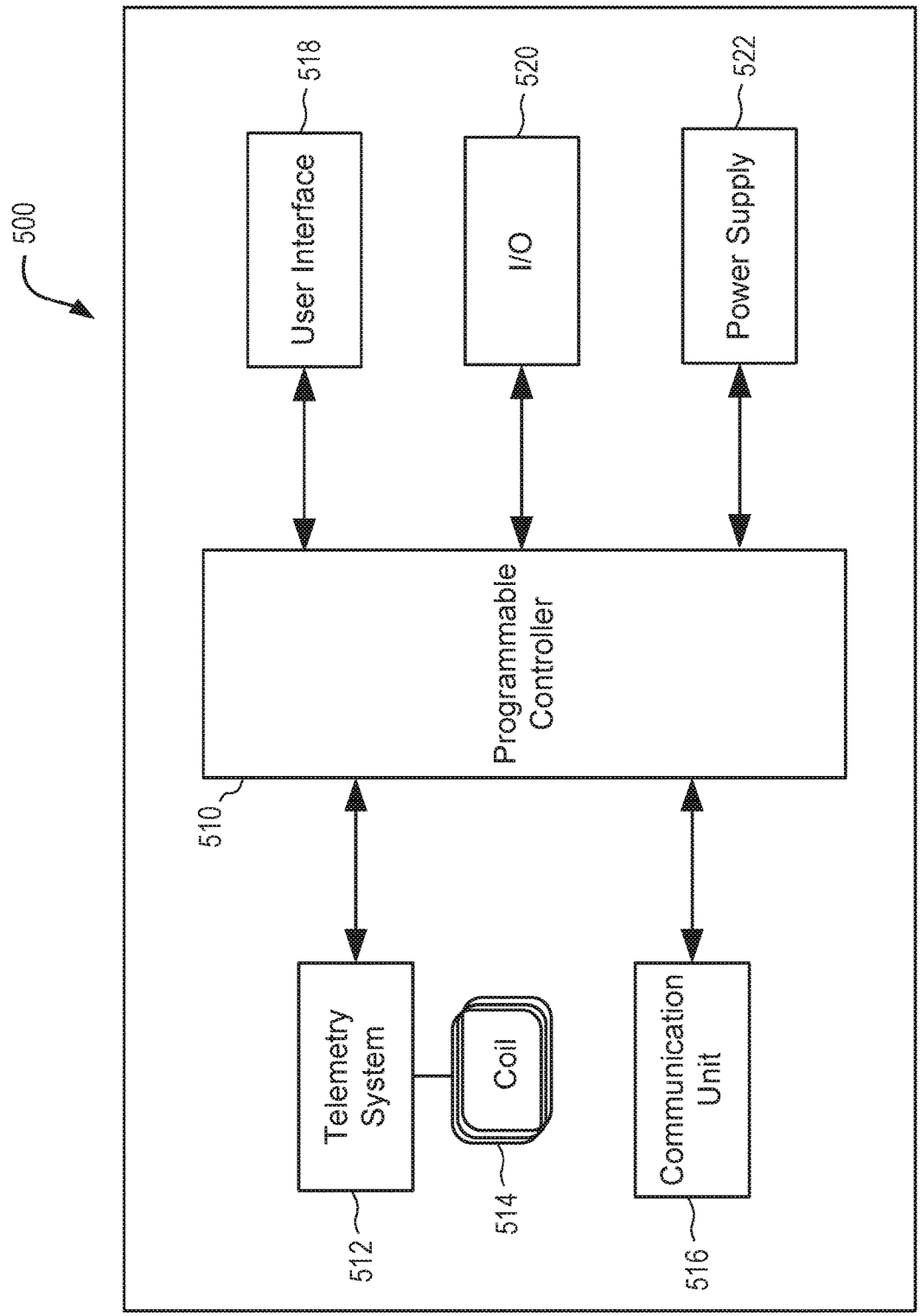
FIG. 5 shows a generalized block diagram of an exemplary external monitoring component of the system of FIG. 1.

Referring to FIG. 5, a generalized schematic diagram of the internal functional components of external monitoring component 500 is now described. External monitoring component 500 may include programmable controller 510, telemetry system 512 coupled to inductive coil 514, communication unit 516, user interface 518, input and output circuitry (I/O) 520, and power supply 522.

Programmable controller 510 is electrically coupled to, and configured to control, the internal functional components of external monitoring component 500. Controller 510 may comprise one or more commercially available microcontroller units that may include a programmable microprocessor, volatile memory, nonvolatile memory such as EEPROM for storing programming, and nonvolatile storage, e.g., Flash memory, for storing firmware and a log of system operational parameters and patient data. The memory of controller 510 stores program instructions that, when executed by the processor of controller 510, cause the processor and the functional components of external monitoring component 500 to provide the functionality ascribed to them herein. Controller 510 is configured to be programmable such that programming data is stored in the memory of controller 510 and may be adjusted using monitoring system 400. As will be readily understood to one skilled in the art, while FIG. 5 is illustrated to show one programmable controller, multiple programmable controllers may be utilized. Controller 510 may store program routines in its memory. For example, controller 510 may store a routine configured to periodically determine whether sensed parameters were received from implantable component 200 by a predetermined time limit and, if not, send an alert to the user and/or clinician.

Controller 510 is coupled to communications circuitry including telemetry system 512, which is electrically coupled to coil 514, that permits transmission of commands, and optionally power, to sensors 222, 224 within implantable component 200 and receipt of signals indicative of parameters sensed by sensors 222, 224. For example, in an embodiment where sensor 222 is a pressure sensor, controller 510 may cause, responsive to user input at user interface 518, telemetry system 512 to wirelessly power sensor 222 via coil 514 to cause sensor 222 to sense pressure within reservoir 204. Sensor 222 may transmit a pressure signal indicative of the sensed pressure to external monitoring component 500 via telemetry system 512 and coil 514 or communication unit 516. The technology for telemetry system 512 and coil 514 is well known to one skilled in the art and may include a magnet, a short range telemetry system, a longer range telemetry system (such as using MICS RF Telemetry available from Zarlink Semiconductor of Ottawa, Canada), or technology similar to a pacemaker programmer. Alternatively, coil 514 may be used to transmit power only, and separate radio frequency transmitters may be provided in communication unit 516 for establishing bidirectional or unidirectional data communication with sensors 222, 224, for example, when sensors 222, 224 comprise RFID technology.

Communication unit 516 is configured to transmit information, such as signals indicative of sensed parameters and the like, to a remote location such as a mobile device running mobile application 600 and/or a computer running monitoring system 400. Communication unit 516 may include circuitry; e.g., WiFi, Bluetooth, and/or cellular chipsets; configured for wireless communication over a network such as the Internet, a local network, or a telephone network using techniques known in the art. In one embodiment, controller 510 runs a programmed routine to determine if a sensed parameter is above or below a predetermined threshold and, if so, sends an alert and/or data to the clinician, e.g., via monitoring system 400 or a secure website accessible by the patient's clinician, or to an emergency service to facilitate emergency treatment.

User interface 518 is configured to receive user input and, optionally, to display information to the user. User interface 350 may include buttons for receiving user input and a display for displaying information to the user, e.g., buttons and display of user interface 504 in FIG. 1. As will be readily apparent to one skilled in the art, user interface 518 is not limited thereto and may use one or more of a touch screen, a keypad, a microphone, a speaker, a trackball, or the like. A user may, for example, provide user input by pressing a button to cause controller 510 to direct telemetry system 512 to transmit a command to begin sensing and/or power, via coil 514, to a sensor within implantable component 200. Then, one or more signals indicative of the sensed parameters from the sensor may be received and the display of user interface 518 may display the measured parameter.

Input and output circuitry (I/O) 520 may include ports for data communication such as wired communication with a computer/mobile device and/or ports for receiving removable memory, e.g., SD card, upon which program instructions or data related to external monitoring component 500 use may be stored. In one embodiment, I/O 354 comprises a port, and corresponding circuitry, for accepting a cables to electrically couple external monitoring component 500 to the mobile device running mobile application 600 or to the computer running software-based monitoring system 400.

Power supply 522 powers the electrical components of external monitoring component 500, and may comprise a primary cell or battery, a secondary (rechargeable) cell or battery or a combination of both. Alternatively, power supply 522 may be a port to allow external monitoring component 500 to be plugged into a conventional wall socket for powering components. In one embodiment, power supply 522 comprises one or more ports and one or more cables that enable external monitoring component 500 to be powered from the mobile device running mobile application 600.

Figure 6:
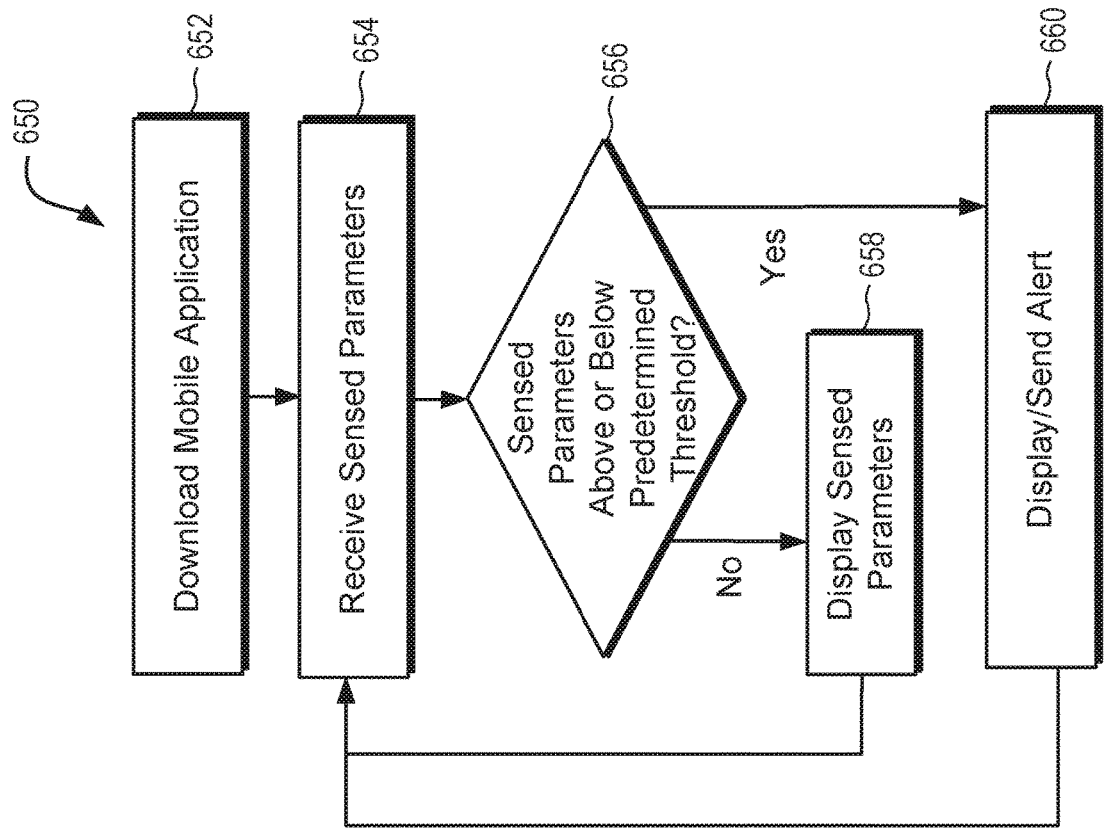
FIG. 6 shows an exemplary method for downloading and using a mobile application in accordance with the principles of the present disclosure.

Referring now to FIG. 6, apparatus and method 650 for downloading and using mobile application 600 on the mobile device are now described. As will be apparent to one of ordinary skill in the art, method 200 may be embodied in program instructions stored on the memory of the mobile device that, when executed by one or more programmable controllers, cause the mobile device to provide the functionality ascribed to them herein. The program instructions may be software downloaded onto the memory of the mobile device. For example, mobile application 600 may be non-transitory computer readable media.

At 652, mobile application 600 is downloaded onto the mobile device. Mobile application 600 may be a dedicated application or "app" and may be downloaded from an online store such as iTunes™ (Apple, Inc., Cupertino, Calif.), the App Store (Apple, Inc.), Google™ Play (Google, Inc., Mountain View, Calif.), the Android™ Marketplace (Google, Inc.), Windows™ Phone Store (Microsoft Corp., Redmond, Wash.), or BlackBerry™ World (BlackBerry, Waterloo, Ontario, Canada). Preferably, mobile application 600 need only be downloaded once—although updates may be downloaded—and the remaining portions of method 650 may be repeated without the need to repeat 652.

At 654, one or more signals indicative of sensed parameters are received at the mobile device from external monitoring component 500. For example, a signal may be received using wireless communication circuitry within the mobile device; e.g., WiFi circuitry, Bluetooth circuitry, cellular circuitry or the like; from corresponding communication circuitry, e.g., communication unit 516, of external monitoring component 500.

At 656, mobile application 600 runs a programmed routine to determine whether each sensed parameter is above a predetermined threshold or below another predetermined threshold. For example, the programmed routine may determine whether the pressure sensed using sensor 222 is above a first predetermined threshold or below a second predetermined threshold, may determine whether the humidity sensed using sensor 224 is above a third predetermined threshold or below a fourth predetermined threshold, and/or may determine whether flow rate measured with a third sensor within reservoir 204 is above a fifth predetermined threshold or below a sixth predetermined threshold, etc. The predetermined thresholds may be stored in a lookup table used with mobile application 600 and the thresholds may be adjusted, e.g., by the clinician using monitoring system 400.

At 658, if the sensed parameter is not above a predetermined threshold and not below another predetermined threshold, the sensed parameter is displayed on the display of the mobile device. The sensed parameter may be displayed as a numerical measurement, a wave form, text, a plot, a chart, a graph, or the like. Multiple sensed parameters may be displayed at one time and the displayed sensed parameters may be real-time measurements. In one embodiment, information indicative of pressure within implantable component 200 is displayed based on the sensed pressure signal. Then, sensed parameters may be continuously received and 654, 656, and 658 continuously repeated.

At 660, if the sensed parameter is above a predetermined threshold or below another predetermined threshold, then an alert is generated. The alert may be displayed on the display of the mobile device and/or may be sent remotely. For example, an alert may be transmitted to the clinician, e.g., for display on the computer running monitoring system 400, or may cause the mobile device to call the clinician or an emergency number for immediate patient assistance. Then, sensed parameters may be continuously received and 654, 656, 658, and 660 continuously repeated.

Referring now to FIGS. 7-11, exemplary screen shots generated by user interface block 410 of monitoring system 400 are described for a system in accordance with the present disclosure. In FIGS. 7-11, various graphical user interfaces may be displayed by clicking on tabs 700 across the top of the page. As should be understood, tabs 700 may be combined onto a single screen or separated in a user friendly manner.

Figure 7:
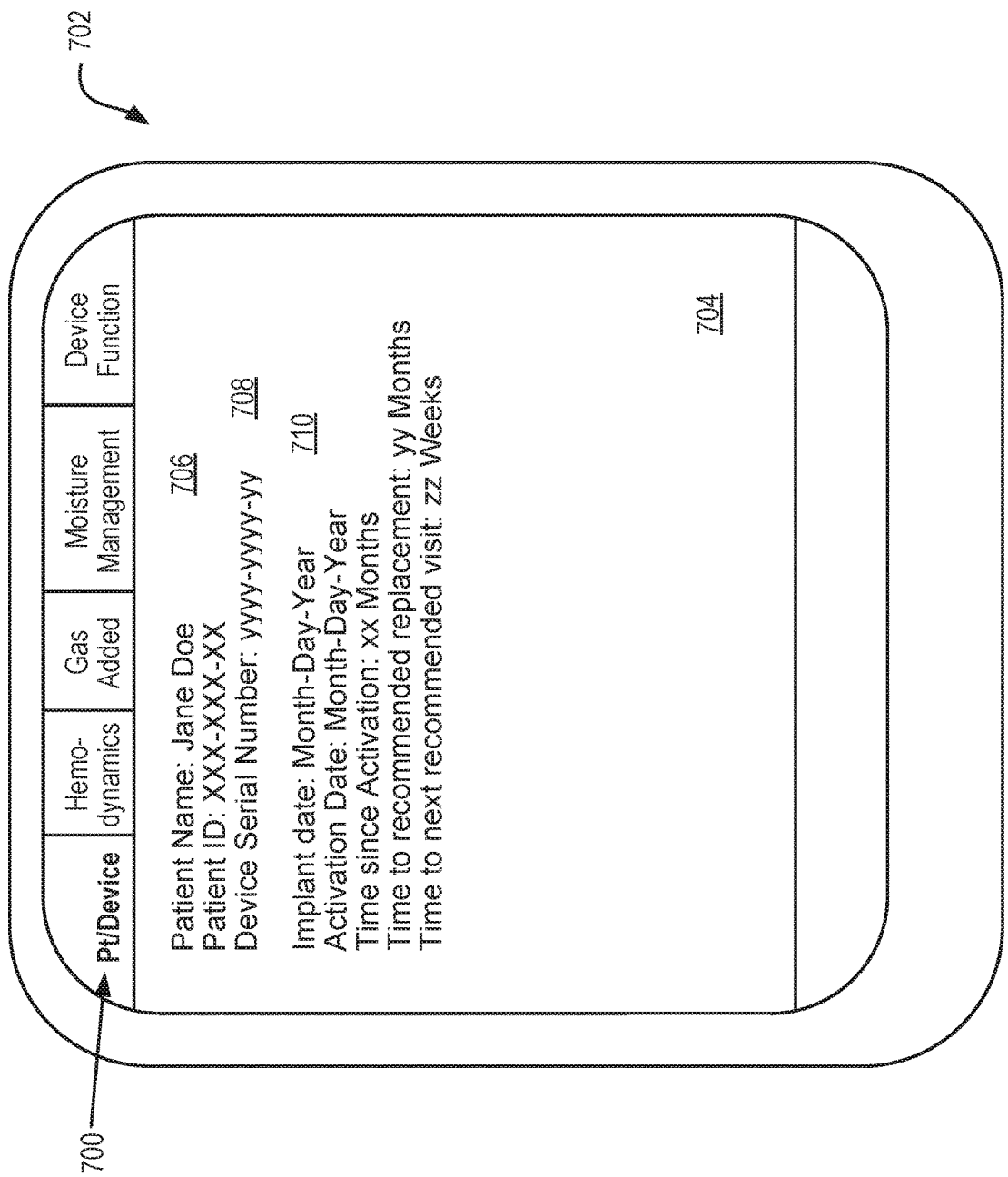
FIGS. 7-11 are exemplary screenshots illustrating various aspects of the graphical user interface of the software-based monitoring system of the present disclosure.

FIG. 7 shows a graphical user interface 704 of patient/device screen 702 that is displayed to a clinician running software-based monitoring system 400. Graphical user interface 704 is configured to display patient information 706, e.g., patient name and patient ID, and implantable component information 708, e.g., device serial number. Patient information 706 and implantable component information 708 may be inputted at User Interface block 410 or scanned into the computer using known techniques such as bar code/RFID scanning. Graphical user interface 704 also may display implant information 710, e.g., implantable component 200 implantation date, implantable component 200 activation date, time since activation, time to recommended replacement, and time to next patient visit. Implant information 710 may be inputted at User Interface block 410 and certain implant information 710 may be calculated based on user input. For example, monitoring system 400 may run routines to determine time since activation based on the activation date, time to recommended replacement based on the implantation and/or activation date, and the time to next patient visit utilizing timing modules known in the art. Patient information 706, implantable component information 708, and implant information 710 may be saved in the memory of the computer running monitoring system 400 or at a suitable database.

Figure 8:
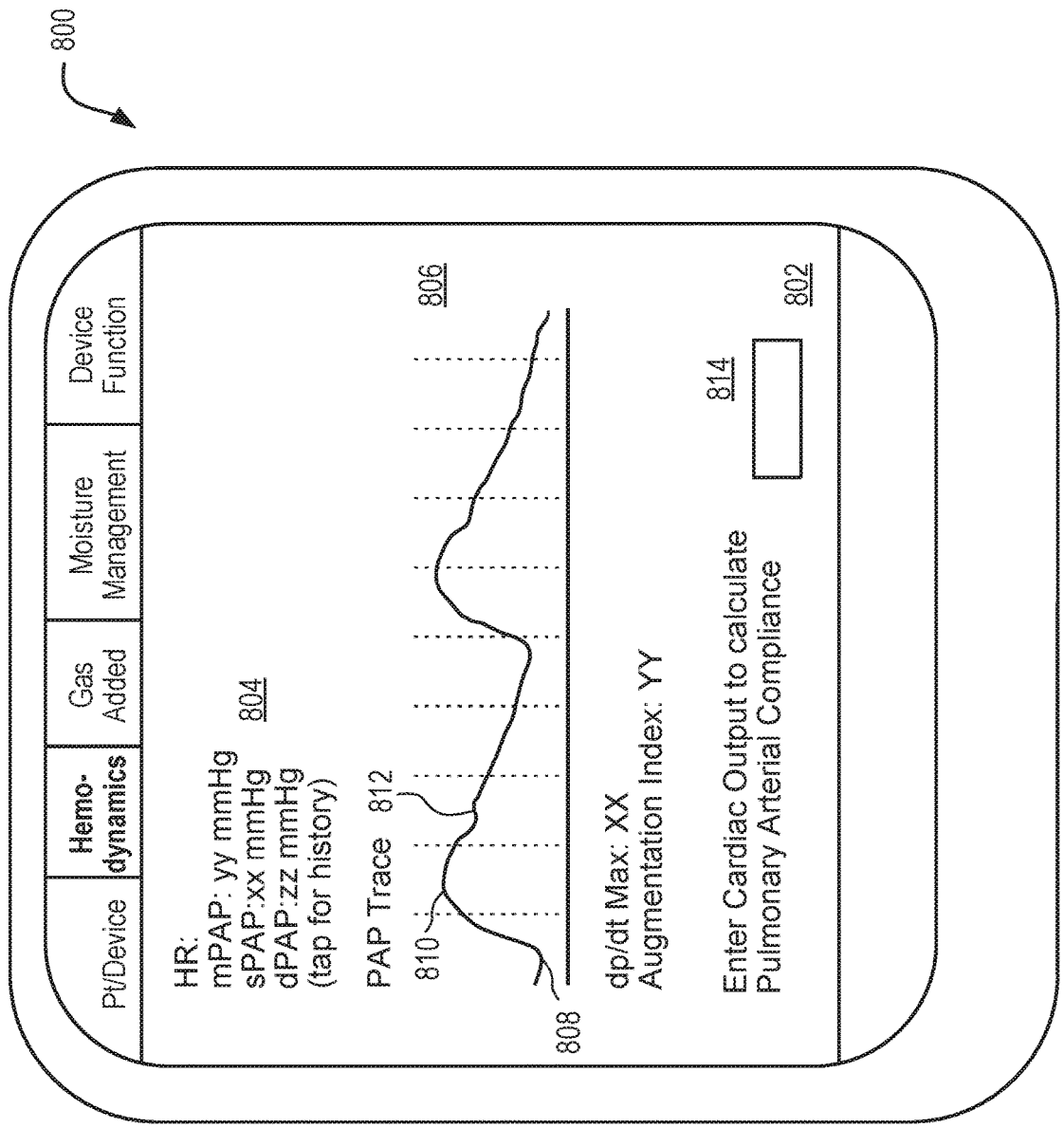

FIG. 8 shows a graphical user interface 802 of hemodynamics screen 800 that is displayed to a clinician running software-based monitoring system 400. Graphical user interface 802 is configured to display pulmonary artery pressure (PAP) information 804, e.g., heart rate (HR), mean pressure (mPAP), systolic pressure (sPAP), and diastolic pressure (dPAP). Graphical user interface 802 further is configured to display pressure plot 806, e.g., PAP waveform trace. Pressure plot 806 illustratively shows pressure versus time during two cardiac cycles. HR, mPAP, sPAP, and dPAP may be calculated using routines programmed in monitoring system 400 based on parameters sensed by system sensors 340 such as pressure within implantable component 200. For example, monitoring system 400 may run routines to determine dPAP using the minimum sensed pressure 808 and to determine sPAP using maximum sensed pressure 810. Graphical user interface 802 may further display the maximum change in pressure over change in time (dp/dt Max) and the Augmentation index. The augmentation index may be calculated using a routine run by monitoring system 400 to divide late systolic pressure 812 by peak systolic pressure 810. Graphical user interface 802 also may display pulmonary artery compliance 814. Monitoring system 400 is configured to run a routine to calculate pulmonary artery compliance based on cardiac output inputted at User Interface block 410. Cardiac output may be determined using echo technology.

Figure 9:
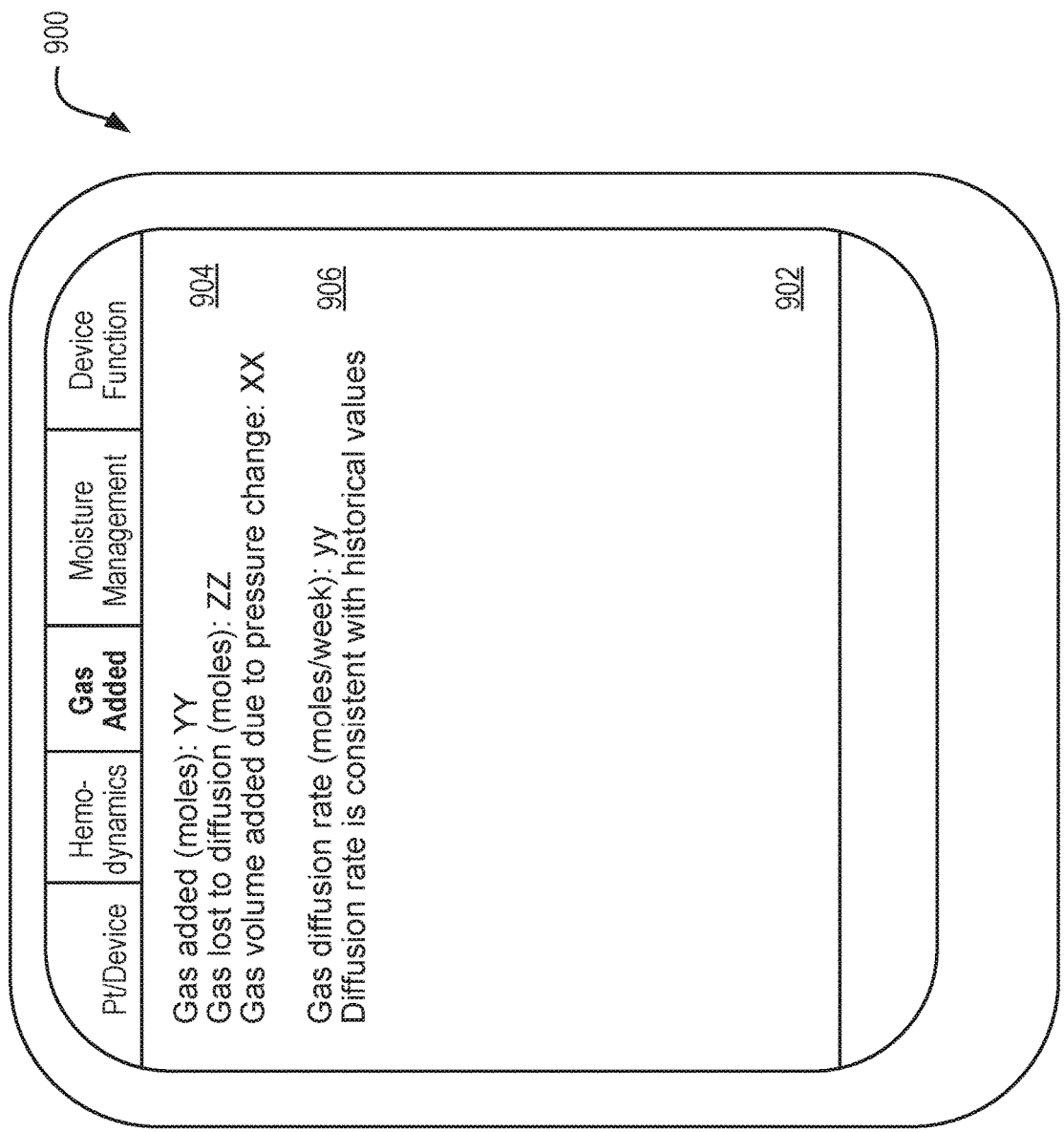

FIG. 9 shows a graphical user interface 902 of gas added screen 900 that is displayed to a clinician running software-based monitoring system 400. Graphical user interface 902 is configured to display fluid information 904, e.g., gas added, gas lost to diffusion, gas volume added due to pressure change. Graphical user interface 902 further is configured to display diffusion information 906, e.g., gas diffusion rate, status alert. Fluid information 904 and diffusion rate 906 may be inputted at User Interface block 410 or may be calculated using routines programmed in monitoring system 400 based on parameters sensed by system sensors 340 such as pressure, volume, and/or flow rate within implantable component 200. If the gas diffusion rate is above a predetermined threshold, graphical user interface 902 may display an alert/alarm.

Figure 10:
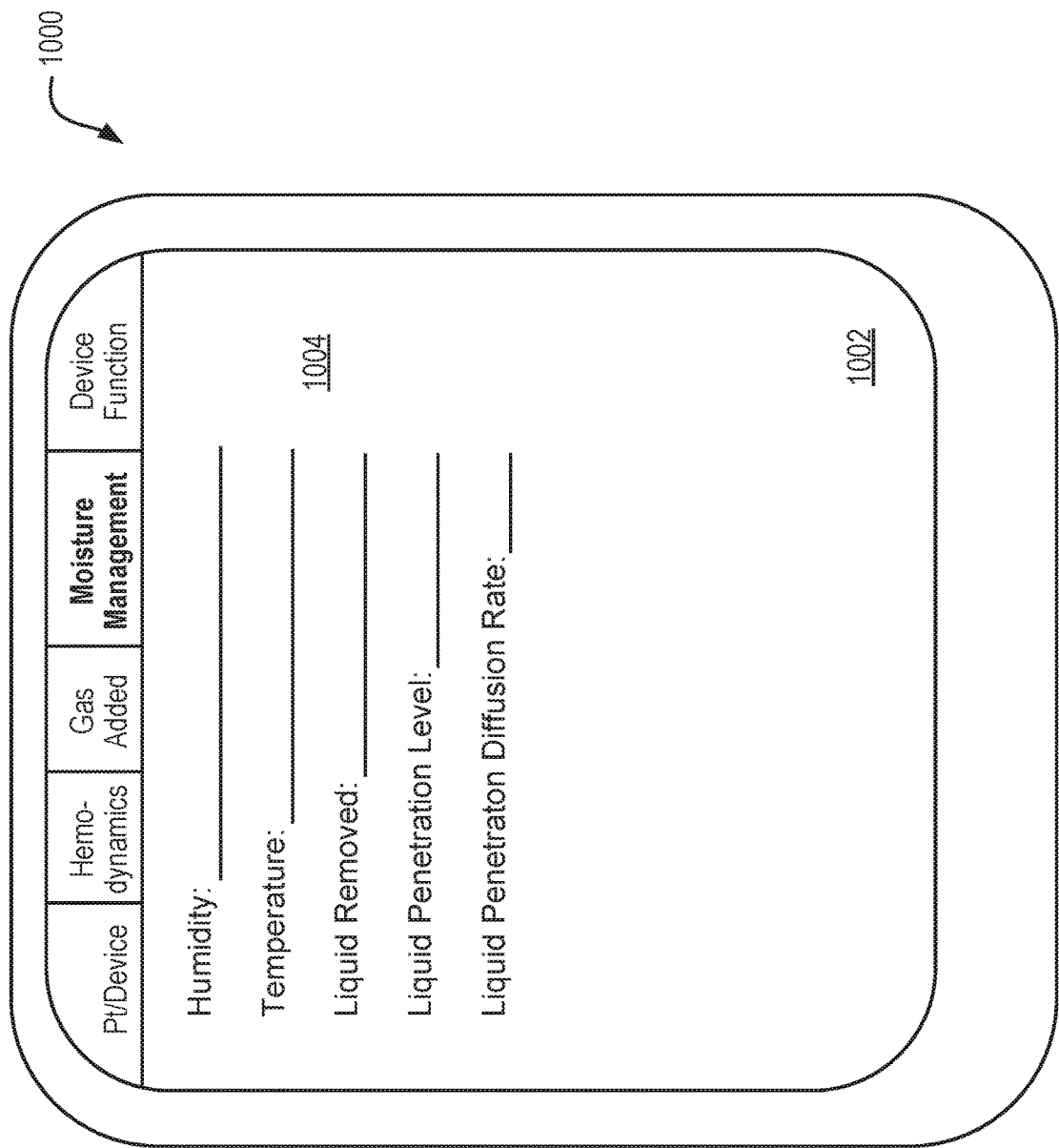

FIG. 10 shows a graphical user interface 1002 of moisture management screen 1000 that is displayed to a clinician running software-based monitoring system 400. Graphical user interface 1002 is configured to display moisture information 1004, e.g., humidity, temperature, liquid removed, liquid penetration level, liquid penetration diffusion rate. Moisture information 1004 may be inputted at User Interface block 410 or may be calculated using routines programmed in monitoring system 400 based on parameters sensed by system sensors 340 such as humidity and temperature within implantable component 200 and volume of injected fluid from and volume of extracted fluid to external clinical controller component 300. If the liquid penetration level is above a predetermined threshold, graphical user interface 902 may display an alert/alarm. In addition, if the liquid penetration diffusion rate is above a predetermined threshold, graphical user interface 902 may display an alert/alarm.

Figure 11:
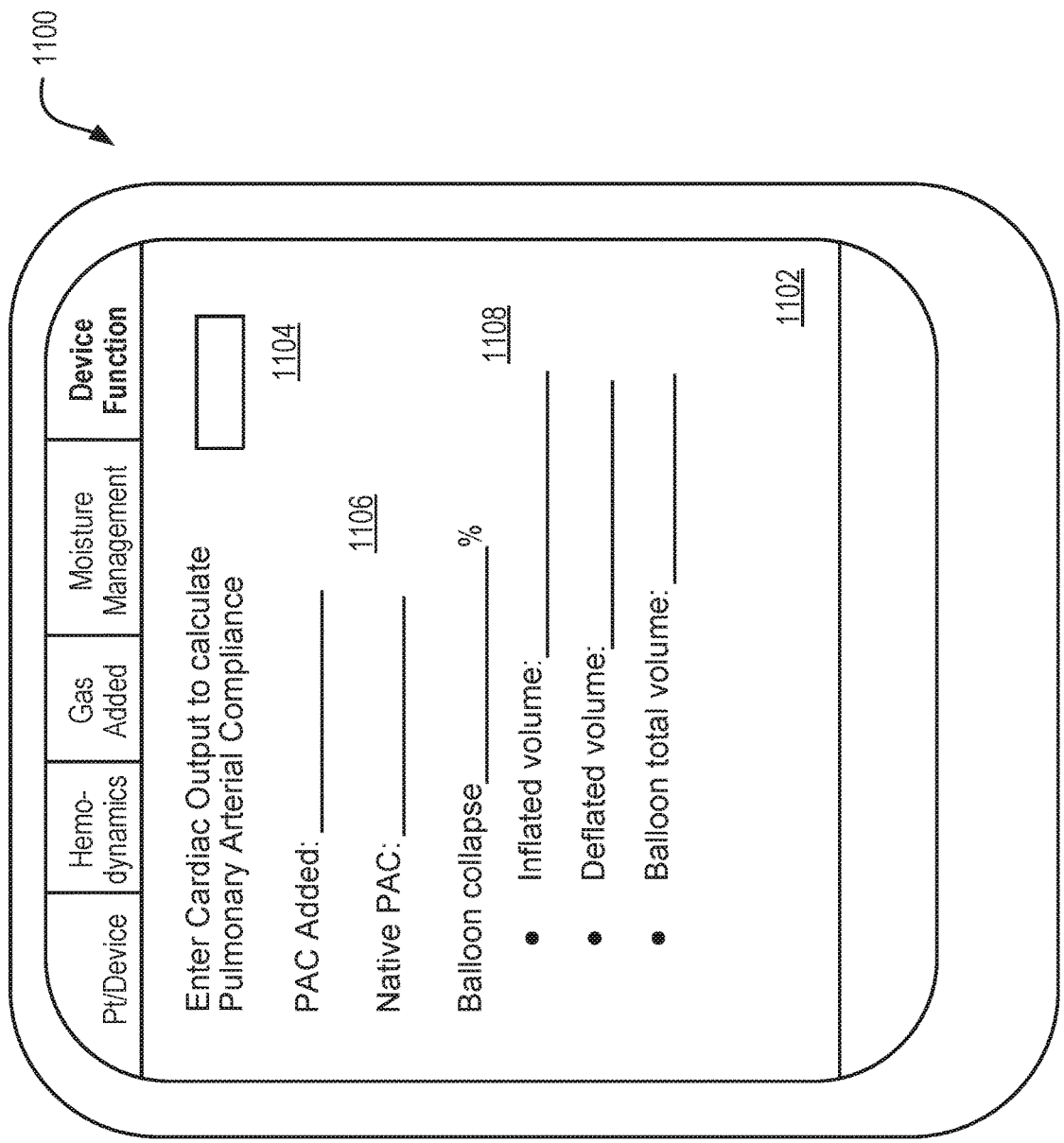

FIG. 11 shows a graphical user interface 1102 of device function screen 1100 that is displayed to a clinician running software-based monitoring system 400. Graphical user interface 1102 may display pulmonary artery compliance 1104. Monitoring system 400 is configured to run a routine to calculate pulmonary artery compliance based on cardiac output inputted at User Interface block 410. Cardiac output may be determined using echo technology. Graphical user interface 1102 also is configured to display PAC information 904, e.g., PAC added, native PAC. PAC information 1106 may be inputted at User Interface block 410 or may be calculated using routines programmed in monitoring system 400. For example, native PAC may be inputted at User Interface block 410 before implantable component 200 is implanted or while deactivated and saved within memory. PAC added may be calculated using a routine to subtract native PAC from PAC calculated at 1104. Graphical user interface 1102 further is configured to display compliant member 202 volume information 1108, e.g., balloon collapse percent, inflated volume, deflated volume, and balloon total volume. Volume information 1108 may be inputted at User Interface block 410 or may be calculated using routines programmed in monitoring system 400 based on parameters sensed by system sensors 340 such as pressure, volume, and/or flow rate within implantable component 200.

As will be readily understood by one of ordinary skill in the art, the displayed information may be displayed in suitable units of measurement. In addition, a user may enter data into the user interface using suitable mechanisms known in the art, such as, entering numbers, letters, and/or symbols via a keyboard or touch screen, mouse, touchpad, selection from a drop-down menu, voice commands, or the like.

Example 1

Figure 12:
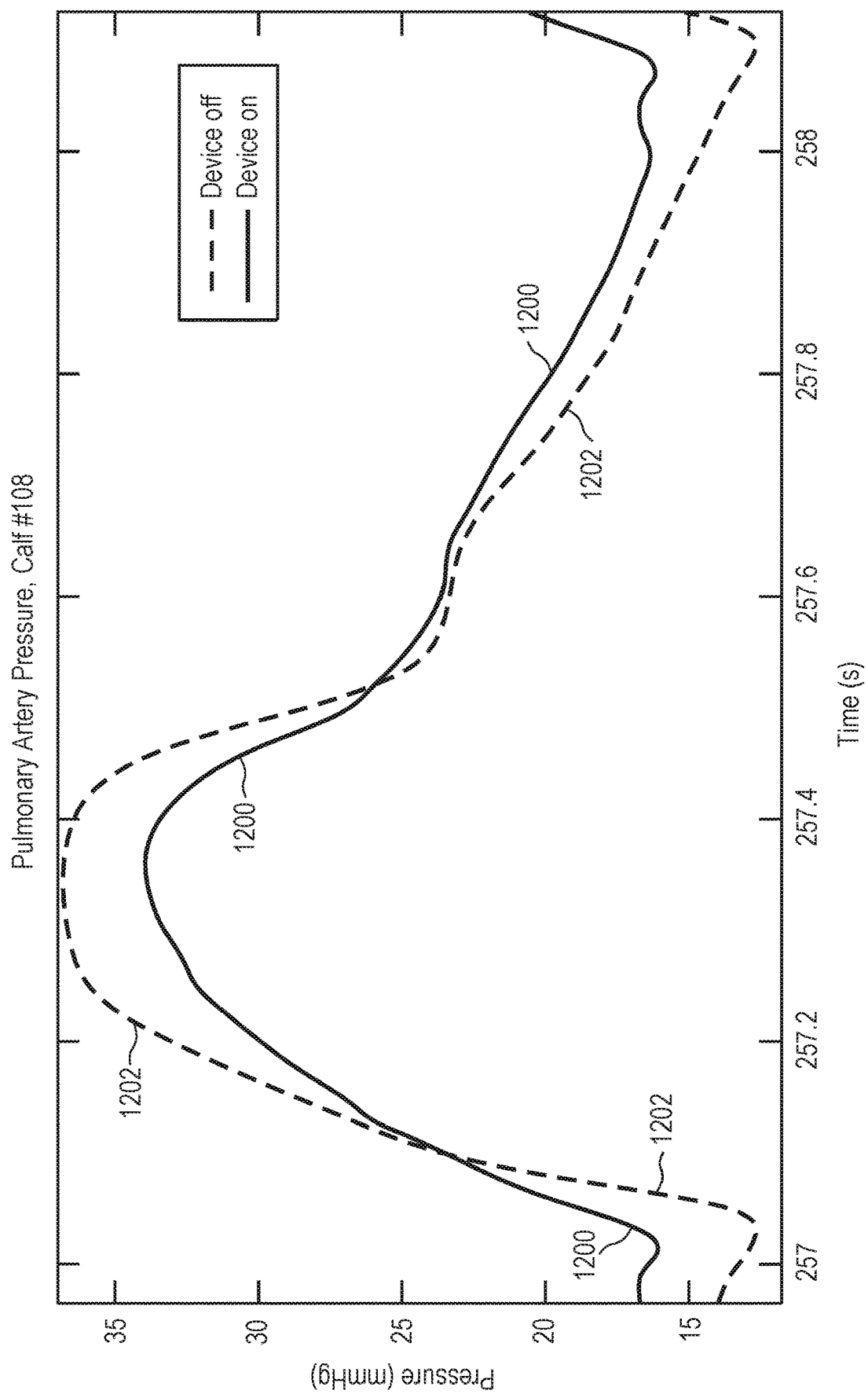
FIG. 12 shows an exemplary plot of pressure over time comparing pulmonary artery pressure of a calf when an implantable component is activated versus deactivated.

Implantable components constructed in accordance with the present disclosure were implanted in calves suffering from altitude-induced PH such that the balloon was positioned in the main pulmonary artery just downstream of the pulmonary valve and inflated and deflated with each cardiac cycle. Altitude-induced PH cattle are widely considered to be the best large animal chronic PH model available. Calves living at altitude on high mountain ranches routinely develop severe hypoxia-induced PH and a significant fraction of them develop Brisket Disease (uncompensated right heart failure). Right heart catheterization and histological examination of these animals have shown hemodynamic performance and small vessel remodeling similar to severe PH in humans. FIG. 12 is a plot illustrating pressure versus time for one calf in the study wherein pressure line 1200, showing pressure when the implantable component is activated, is superimposed over pressure line 1202, showing pressure when the implantable component is deactivated. As may be observed, activation of the implantable component increases diastolic pressure and decreases peak systolic pressure.

Example 2

Figure 13:
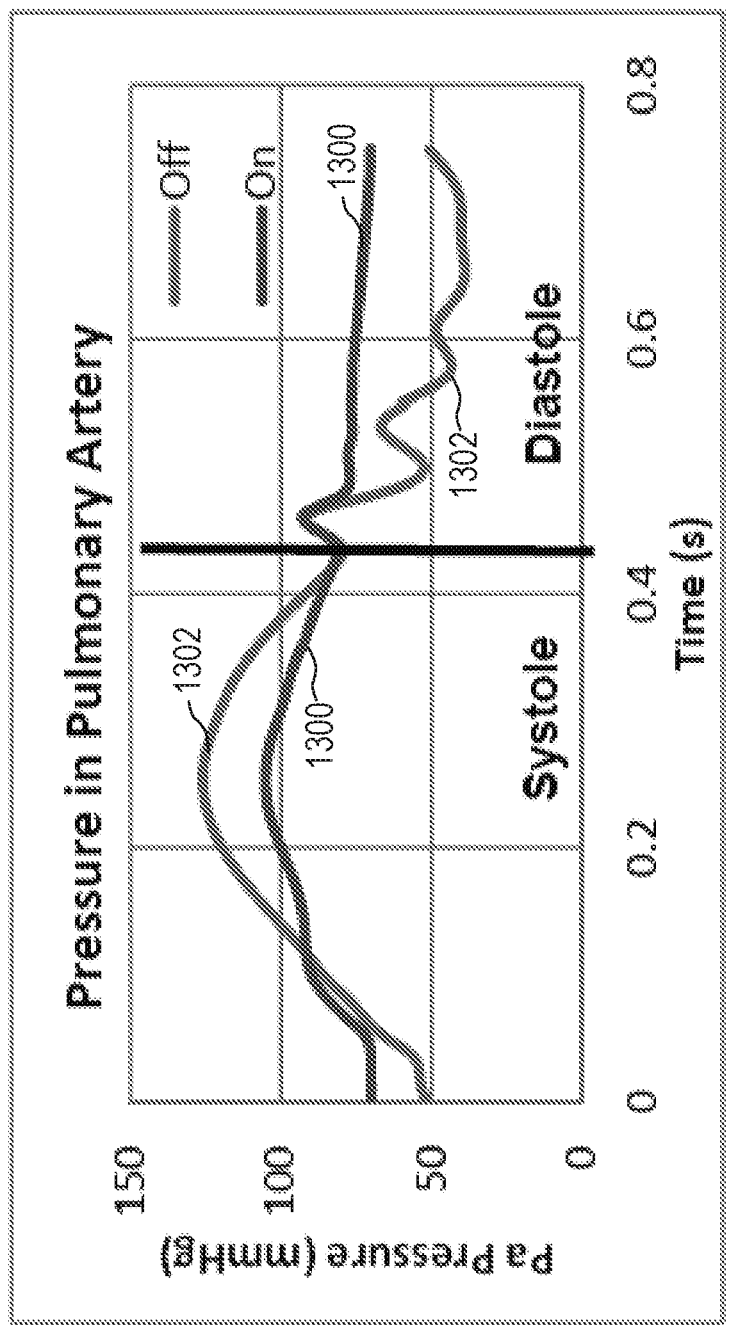
FIG. 13 shows an exemplary plot of pressure over time comparing pulmonary artery pressure in a benchtop design when an implantable component is activated versus deactivated.

FIG. 13 is a plot illustrating pressure versus time using a benchtop model designed to approximate the dimensions and hemodynamic parameters on the right side of the heart and the pulmonary vasculature. In FIG. 13, pressure line 1300 shows pressure when the implantable component is activated while pressure line 1302 (superimposed over pressure line 1300) shows pressure when the implantable component is deactivated. In this example, a reduction of 17% in peak arterial pressure was achieved upon implantable component activation with a 0.9 ml/mmHg increase in compliance. As may be observed, activation of the implantable component increases diastolic pressures and decreases systolic pressures.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for treating pulmonary hypertension, the system comprising:
    a balloon sized and shaped to be implanted in a pulmonary artery, the balloon configured to expand and contract responsive to pressure changes in the pulmonary artery;
    a reservoir in fluidic communication with the balloon;
    a conduit fluidicly coupling the balloon and the reservoir; and
    an implantable anchor configured to transition between a contracted state and an expanded deployed state for securing the balloon within the pulmonary artery, the implantable anchor formed from a shape memory material and configured to self-expand upon deployment within the pulmonary artery, the implantable anchor comprising a plurality of petals spaced around a circumference at a distal end of the implantable anchor.

2. The system of claim 1, wherein the reservoir is adapted to be implanted subcutaneously.

3. The system of claim 1, wherein the balloon is configured to be detachable from at least a portion of the implantable anchor in vivo such that the balloon is replaceable while at least the portion of the implantable anchor remains implanted.

4. The system of claim 1, wherein the implantable anchor is coupled to the conduit distal to the balloon.

5. The system of claim 1, wherein the shape memory material is nitinol.

6. The system of claim 1, further comprising an external clinical controller comprising a fluidic connector configured to be coupled to the reservoir for introduction of fluid into the reservoir.

7. The system of claim 6, wherein the external clinical controller further comprises a fluid source configured to hold the fluid to be introduced into the reservoir through the fluidic connector when the fluidic connector is in fluidic communication with the reservoir.

8. The system of claim 7, wherein the external clinical controller further comprises a fluid movement mechanism configured to move the fluid from the fluid source through the fluidic connector or to extract fluid from the reservoir through the fluidic connector or both.

9. The system of claim 7, wherein the fluid in the fluid source is pressurized, wherein a lumen of the fluidic connector includes a valve, and wherein actuation of an actuator opens the valve such that fluid moves from the fluid source through the fluidic connector.

10. The system of claim 6, wherein the fluidic connector comprises a needle adapted to be inserted into a septum of the reservoir to achieve fluidic communication with the reservoir.

11. The system of claim 6, wherein the fluid introduced by the external clinical controller comprises nitrogen or carbon dioxide.

12. The system of claim 6, wherein the fluid introduced by the external clinical controller is selected to reduce diffusion through the balloon.

13. The system of claim 1, further comprising an external clinical controller comprising a sensor configured to generate a parameter signal indicative of a parameter of the system.

14. The system of claim 13, wherein the parameter comprises pressure within the reservoir, temperature within the reservoir, humidity within the reservoir, fluid flow rate within the reservoir, fluid diffusion rate, amount of extracted fluid from the reservoir, fluid concentration within the reservoir, or pH within the reservoir, or any combination thereof.

15. The system of claim 13, further comprising software configured to run on a computer operatively coupled to the sensor, the software configured to cause a graphical user interface to display information indicative of the parameter based on the parameter signal.

16. A method for implanting a system for treating pulmonary hypertension, the method comprising:
    delivering an implantable anchor to a pulmonary artery, the implantable anchor configured to be coupled to a balloon configured to be fluidicly coupled to a reservoir via a conduit, the implantable anchor comprising a plurality of petals spaced around a circumference at a distal end of the implantable anchor; and
    deploying the implantable anchor from a contracted state within the pulmonary artery such that the implantable anchor self-expands to an expanded deployed state wherein the plurality of petals of the implantable anchor contacts an inner wall of the pulmonary artery for securing the balloon within the pulmonary artery, the balloon configured to expand and contract responsive to pressure changes in the pulmonary artery to treat pulmonary hypertension.

17. The method of claim 16, wherein the implantable anchor is coupled to the conduit distal to the balloon.

18. The method of claim 16, further comprising, after deploying the implantable anchor, coupling the balloon to the implantable anchor.

19. The method of claim 16, further comprising:
    coupling a fluidic connector of an external clinical controller to the reservoir; and
    introducing fluid from the external clinical controller via the fluidic connector to the reservoir.

20. The method of claim 19, further comprising:
    sensing a parameter via a sensor associated with the external clinical controller; and
    displaying information indicative of the parameter based on a signal from the sensor.

21. The method of claim 16, further comprising subcutaneously implanting the reservoir.

* * * * *